US008303522B2

(12) United States Patent
Apperson et al.

(10) Patent No.: US 8,303,522 B2
(45) Date of Patent: Nov. 6, 2012

(54) DEVICE FOR TRANSFECTING CELLS USING SHOCK WAVES GENERATED BY THE IGNITION OF NANOENERGETIC MATERIALS

(75) Inventors: Steve Apperson, Columbia, MO (US); Shubhra Gangopadhyay, Columbia, MO (US); Luis Polo-Parada, Columbia, MO (US); Andrey Bezmelnitsyn, Columbia, MO (US); Keshab Gangopadhyay, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 798 days.

(21) Appl. No.: 12/253,706

(22) Filed: Oct. 17, 2008

(65) Prior Publication Data
US 2009/0105738 A1    Apr. 23, 2009

Related U.S. Application Data

(60) Provisional application No. 60/980,901, filed on Oct. 18, 2007.

(51) Int. Cl.
*A61H 1/00* (2006.01)
(52) U.S. Cl. .......................................... 601/2
(58) Field of Classification Search .............. 604/22; 601/2, 4; 600/437, 439
See application file for complete search history.

(56) References Cited

U.S. PATENT DOCUMENTS

| 4,813,402 A * | 3/1989 | Reichenberger et al. ......... 601/4 |
| 4,893,614 A | 1/1990 | Takayama et al. |
| 6,539,869 B2 | 4/2003 | Knowlton et al. |
| 2005/0232817 A1 | 10/2005 | Ahn et al. |

FOREIGN PATENT DOCUMENTS

| WO | 2007053397 A2 | 5/2007 |
| WO | 2007053543 A2 | 5/2007 |
| WO | WO 2007/053397 A2 * | 5/2007 |
| WO | WO 2007/053542 A2 * | 5/2007 |

OTHER PUBLICATIONS

ISR dated Dec. 24, 2008 regarding PCT/US2008/080332, two (2) pages.
Doukas et al, Transdermal drug delivery with a pressure wave, Advanced Drug Delivery Reviews, 2004, pp. 559-579, vol. 56.
Apperson et al, Nanoenergetic Reactions for Medical Applications, Poster, one (1) page.
Apperson et al, Shockwave-Induced Cell Transfection Using Energetic Materials, Poster, one (1) page.

* cited by examiner

*Primary Examiner* — Manuel Mandez
(74) *Attorney, Agent, or Firm* — Polsinelli Shughart PC

(57) ABSTRACT

A miniature device for generating shock waves using the energy of combustion of a nanoenergetic material and directing the shock waves into biological tissues is described.

32 Claims, 26 Drawing Sheets

DEVICE FOR TRANSFECTING CELLS USING SHOCK WAVES GENERATED BY THE IGNITION OF NANOENERGETIC MATERIALS

CROSS REFERENCE TO RELATED APPLICATION

This application claims priority from U.S. provisional patent application Ser. No. 60/980,901, entitled "Device for Transfecting Cells Using Shock Waves Generated by the Ignition of Nanoenergetic Materials" filed on Oct. 18, 2007.

GOVERNMENTAL RIGHTS

This work may have been partially supported by the U.S. Office of Naval Research grant entitled "MEMS-Based System for Shockwave Generation without Detonation", grant number N00014-06-1-0368. The U.S. government may have certain rights in this invention.

FIELD OF THE INVENTION

The present invention is related to devices that create pressure waves and direct the pressure waves into biological tissues. In particular the present invention is related to a miniature device that generates shock waves from the ignition of nanoenergetic material, and directs the resulting shock waves into biological tissues. The shock waves may be used to deliver compounds such as pharmaceutical compounds and genetic materials to biological cells and tissues.

BACKGROUND OF THE INVENTION

Pressure waves have been used for many biological applications including the destruction of kidney stones (lithotripsy), the delivery of drug compounds and imaging particles to cells and tissues, gene therapy, cancer treatment, insulin and allergen delivery, and the modification of tissues. Many of these biological applications were achieved due to the ability of the energy carried by pressure waves to permeabilize the epidermis, cell plasma membranes, and cell nuclear envelopes, thereby creating a temporary pathway through which the desired molecules were able to penetrate these barriers.

Existing devices generate pressure waves using energy sources such as laser pulses, rapid diaphragm releases, compressed gas, electrostatic discharges, or by initiation of microexplosions. The characteristics of the pressure waves differ from device to device, and are critical to the effectiveness of these devices in biological applications.

Shock waves are pressure waves that are generated by a source moving faster than the speed of sound in the medium carrying the shock waves. The effects of the forces induced by the impingement of shock waves on cells and tissues depend on the characteristics of the shock waves, including rise time, peak pressure, and pressure impulse. For example, shock waves possessing short rise times, high peak pressures, or high pressure impulses have been correlated with a high degree of cell permeabilization.

However, shock waves may cause cell injury or destruction if the peak pressure or the pressure impulse exceeds a threshold level. Although the threshold for cell injury appears to be higher than the threshold for cell permeabilization, the thresholds for permeabilization and cell injury vary as a function of the particular cell line and molecules being introduced to the cells. For biological applications, the ability to fine-tune the characteristics of the shock waves to fall between the threshold of permeabilization and the threshold for cell damage would enhance the utility of a device using shock waves to deliver compounds to cells.

Existing devices are relatively large in size and the controllability of the shock wave parameters such as peak pressure, pressure impulse and rise time are limited. Laser-generated shock waves possess high peak pressures, but the pressure impulses of the shock waves are limited due to the durations of these shock waves, which are on the order of nanoseconds. Gas-generated shock waves have a longer duration in the range of microseconds, but the peak pressure is relatively limited. Shock waves may also be created using the detonation of energetic materials such as lead azide. However, heavy-metal azides are sensitive to accidental detonation, and lead-based materials are environmentally hazardous, severely limiting the utility of heavy-metal azide detonation as a technique of generating pressure waves in biological applications.

A need exists for a suitably small device that generates shock waves with high peak pressures, fast rise times, and high pressure impulses, with the added ability to fine-tune the characteristics of the shock waves to match the requirements of individual cell types and compounds to be delivered.

SUMMARY OF THE INVENTION

The present invention provides a miniature device for creating and directing at least one shock wave into biological targets, wherein the at least one shock wave has a peak pressure of up to 200 MPa and duration of up to 100 microseconds. The miniature device includes an amount of energetic material, and a transmissive barrier. The transmissive barrier propagates the at least one shock wave and also prevents the byproducts of combustion of the nanoenergetic material from contacting the biological targets.

The present invention also provides a miniature device for creating and directing at least one shock wave into biological targets, wherein the at least one shock wave has a peak pressure of up to 200 MPa and duration of up to 100 microseconds that includes a substrate that includes opposed surfaces and at least one igniter bonded to one surface of the substrate. The miniature device also includes an amount of nanoenergetic material placed on one surface of the substrate in contact with the at least one igniter and a transmissive barrier that is placed in close proximity to the amount of nanoenergetic material, opposite to the surface of the substrate.

The present invention also provides a miniature device for creating and directing at least one shock wave into biological targets, wherein the at least one shock wave has a peak pressure of up to 200 MPa and duration of up to 100 microseconds that includes a substrate comprising opposed surfaces, at least one igniter bonded to one surface of the substrate layer, and an amount of nanoenergetic material placed on one surface of the substrate in contact with the at least one igniter. In addition, the miniature device includes at least one tubular member that has two opposed openings and a lumen. One opening of the tubular member is placed in close proximity to the nanoenergetic material, opposite to the surface of the substrate. A gel is placed inside the lumen of the tubular member.

The present invention also provides a miniature device for creating and directing at least one shock wave into biological targets, wherein the at least one shock wave has a peak pressure of up to 200 MPa and duration of up to 100 microseconds that includes a substrate comprising opposed surfaces, at least one igniter bonded to one surface of the substrate layer, and an amount of nanoenergetic material placed on one surface of the substrate in contact with the at least one igniter. In addition, the miniature device includes a flexible membrane that is bonded one surface of the substrate over the amount of nanoenergetic material.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the views of the drawings. The headings used in the figures should not be interpreted to limit the scope of the claims.

DETAILED DESCRIPTION OF THE INVENTION

The present invention is directed to a miniature device that creates and directs shock waves into biological targets, for example to implement the transfection of cells with an amount of genetic material. The miniature device generates shock waves with profiles characterized by high peak pressures and high pressure impulses simultaneously, resulting in the ability to transfect cells with relatively high efficiency compared to existing chemical and electrical transfection techniques. The present invention is capable of generating shock waves with peak pressures of up to 1200 MPa, pressure impulses of up to 20,000 Pa-s, and durations of up to 100 microseconds. The measured performance of the device may vary depending on the particular configuration of the device and the equipment used to measure the shock wave profiles, as illustrated in the examples below.

The survivability of cells transfected using the miniature device typically ranges between about 95% and about 99%. Further, the shock wave profiles may be adjusted by changing the amount or composition of the nanoenergetic material to tailor the shock wave characteristics to meet specific biomedical applications. Thus, the device of the present invention provides high levels of shock wave intensity and pressure impulse, coupled with the ability to vary or control the peak intensity, pressure impulse, timing, or spatial extent of the shock waves as needed.

The miniature device of the present invention integrates nanoengineered energetic materials and microchip technology, resulting in a controlling and repeatable miniature shock wave generator. The device of the present invention may be of a variety of constructions including a bench-top laboratory device for in vitro applications, a catheter-mounted device for the treatment of internal cells and tissues, and externally-applied devices for the transdermal or transmucosal administration of therapeutics.

The elements of the miniature device are described in detail below. In addition, a method of fabricating the miniature device of the present invention and a method of delivering a compound to a biological tissue using the device of the present invention are described below.

A. Overview of Miniature Device

Figure 1:
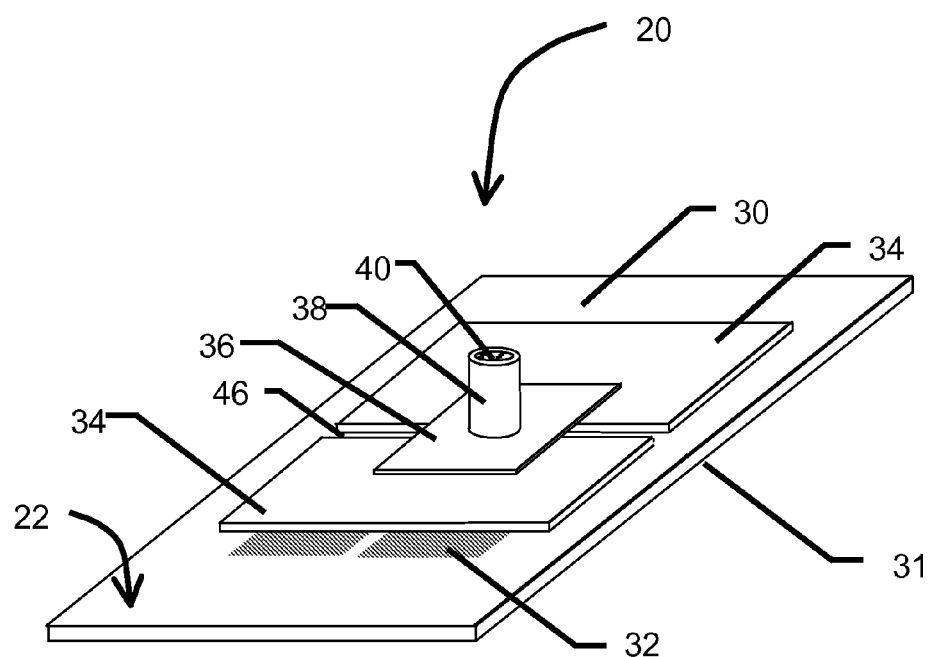
FIG. 1 is an oblique drawing of the miniature shock wave generating device.

The device requires nanoenergetic material and a transmissive barrier. Variations of the miniature device can be developed but the miniature device illustrated in FIG. 1 is exemplary. Referring to FIG. 1, the miniature device 20 includes a substrate 22, a structural layer 34, a flexible membrane 36, a tubular member 38 filled with a gel 40, and an igniter 32 in one embodiment. The substrate 22 is a planar sheet fabricated from a rigid material. The substrate 22 provides structural support for the miniature device 20 and includes an upper surface 30 and a lower surface 31. At least one igniter 32 may also be bonded to the upper surface 30 of the substrate 22.

Figure 2:
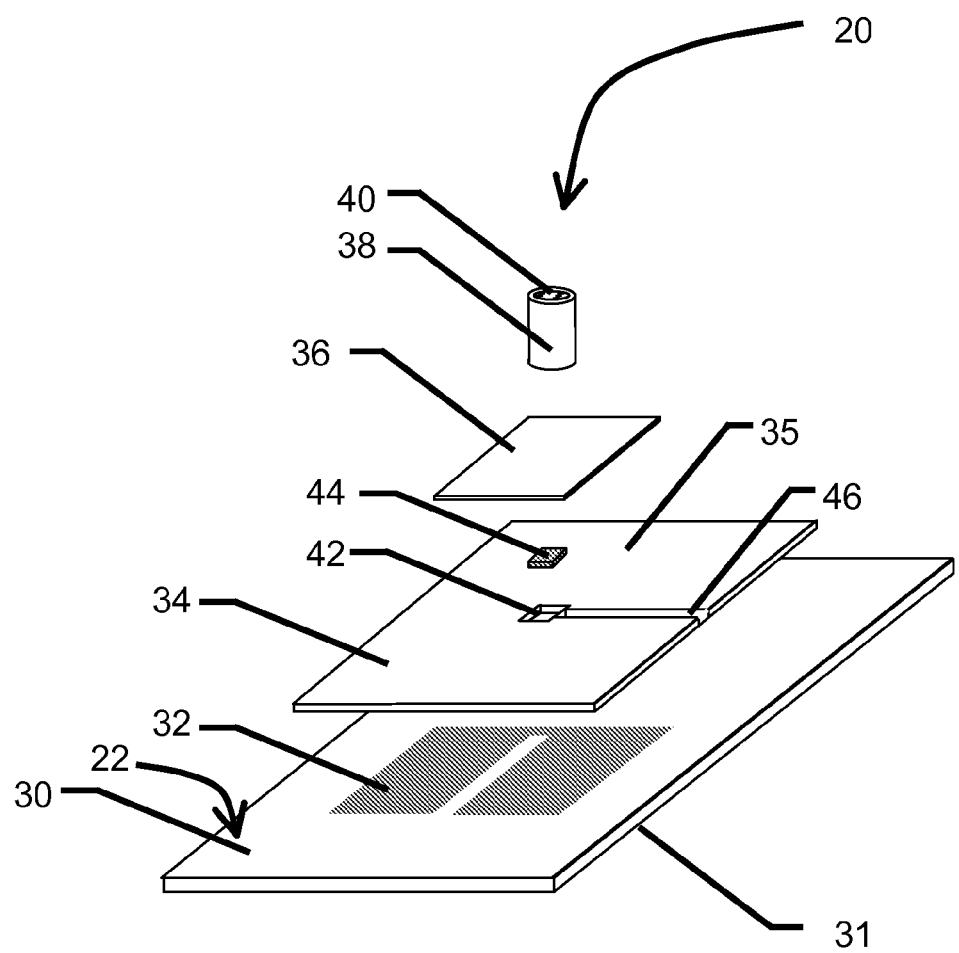
FIG. 2 is an exploded view drawing of the miniature shock wave generating device.

The igniter 32 can be of a variety of constructions so long as the nanoenergetic material is activated to provide a suitable explosion. Many variations of the construction of the igniter 32 may be developed, but FIG. 2 is exemplary. Referring to FIG. 2, the igniter 32 may include two connection pads 35 electrically connected to the opposing ends of a fuse wire 33. The structural layer 34 forms the sides of at least one well 42. The structural layer 34 is bonded to the substrate 22 such that the at least one well 42 is centered over the fuse wire 33 of the at least one igniter 32. The bottom of the at least one well 42 is formed by the upper surface 30 of the substrate 22.

The miniature device 20 also includes an amount of energetic material 44 such as a mixture of $Bi_2O_3$ and aluminum nanoparticles fitted inside the at least one well 42. The flexible membrane 34 is attached to the upper surface 45 of the structural layer 34, over the energetic material 44 in the at least one well 42.

Detailed descriptions of the substrate 22, structural layer 34, flexible membrane 36, tubular member 38, gel 40, energetic material 44, and igniter 32 are given below.

1. Transmissive Barrier

The transmissive barrier 35 transmits the shock wave pressures generated by the combustion of the energetic material 44 to the biological tissue to be treated. In addition, the transmissive barrier 35 prevents the by-products from the combustion of the energetic material 44 from escaping the device 20 and contaminating the biological tissue. The transmissive barrier 35 may include a substrate 22, a structural layer 34 defining at least one well 42, a flexible membrane 36, a tubular element 38 filled with a gel 40, and combinations thereof.

2. Substrate

The substrate 22 is typically a planar sheet structural member that provides a rigid support for the other elements of the miniature device 20. The size of the substrate 22 may vary, with a thickness of up to about 10 mm and the maximum dimension between about 10 mm and about 50 mm. The substrate 22 may be constructed of materials selected from the group including glass, polycarbonate thermoplastic, stainless steel, silicon, and acrylic. The substrate 22 may be fabricated from any other rigid material, so long as the material may receive and hold other members, is resistant to high temperatures, and is not reactive with the energetic material 44. The substrate 22 has opposed sides or faces including an upper surface 30, and a flat lower surface 31, for resting on a surface. The substrate 22 typically has a rectangular or square construction.

The upper surface 30 may form a flat shape, as shown in FIG. 1, or the upper surface may form a concave or convex shape. Without being bound to any particular theory, the shape of the upper surface 30 may act to direct the at least one shock wave formed by the ignition of the energetic material 44 in the at least one wells 42 in a predetermined direction. The shape of the upper surface 30 may focus multiple shock waves to a single point in space, or the upper surface 30 may focus multiple shock waves into a planar combined shock wave.

i. Igniter

Figure 3:
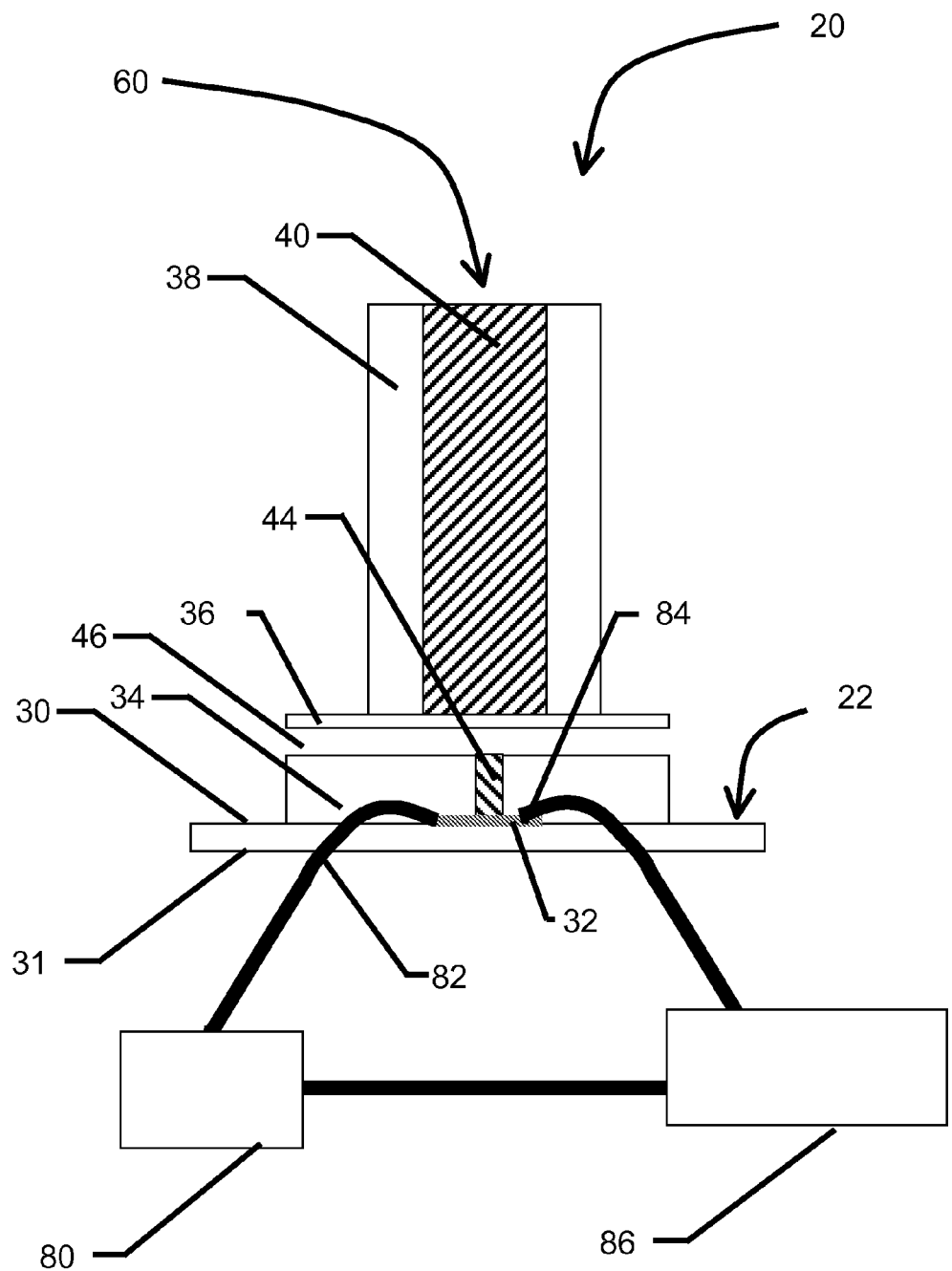
FIG. 3 is a cross-sectional side view drawing of the miniature shock wave generating device.

The igniter 32 generates heat that induces the ignition of the energetic material 44. The igniter 32 includes two connection pads 35 that are electrically connected to the opposing ends of a fuse wire 33. The fuse wire 33 is typically a thin filament designed and dimensioned to offer high resistance to electrical flow. Without being bound to any particular theory, when a power source is attached to the igniter 32 as described below, the high resistance fuse wire 33 generates heat that ignites the energetic material 44 in the well 42. The connection pads 35 are designed and dimensioned to facilitate the connection of power leads 82 using soldering or other wire joining techniques known to the art, in order to electrically connect the miniature device 20 to a power source 80 and ignition controller 86, as shown in FIG. 3.

The materials used to fabricate the igniter 32 are selected from the group including titanium, platinum, gold, silver, steel, aluminum and combinations thereof. The igniter 32 may be fabricated in a separate process and then bonded to the substrate 22, or the igniter 32 may be fabricated directly onto the substrate 22. In an embodiment, the igniters 32 may be formed on a glass substrate 22 using photoresist lift-off patterning and sputter deposition of Pt/Ti thin films or other methods known in the art.

Figure 4:
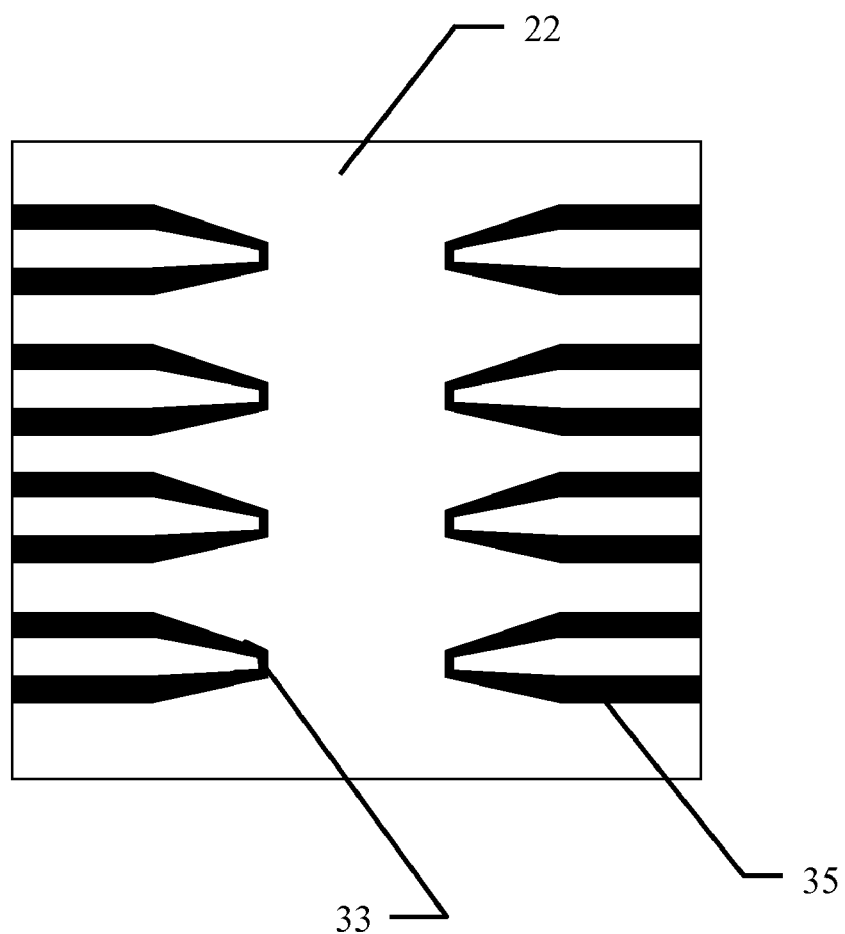
FIG. 4 is a top view of an array of igniters in accordance with an embodiment of the present invention.

The miniature device 20 may include a single igniter 32 as shown in FIG. 2, or the miniature device may include between about two and about twenty igniters 32. FIG. 4 illustrates an exemplary array of eight igniters 32 integrally formed on the upper surface 30 of the substrate 22.

a. Power Source

The power source is any device electrically connected to the igniter 32 that supplies direct current (DC) electrical power to the igniter 32. Referring to FIG. 3, a power source 80, selected from the group comprising batteries and DC power converters, supplies voltages ranging between about 1V to about 12V DC to the igniter 32. The power source 80 is electrically connected to the igniter 32 by way of power leads 82 attached to the connection pads 35 of the igniter 32.

b. Ignition Controller

The ignition controller is any device that controls the amount of electrical power supplied to the igniter 32 by the power source 80, thereby controlling the combustion of the nanoenergetic material. An ignition controller 86 may be connected into the electrical circuit that includes the igniter 32 and the power source 80. The ignition controller 86 may be selected from the group including a mechanical switch and digital microcontroller devices. The ignition controller 86 and power source 80 may be connected to a single igniter 32, as shown in FIG. 3, or the ignition controller and power source may be connected to an array of igniters such as the array shown in FIG. 4. When connected to an array of igniters, the ignition controller 86 may direct power in a pre-determined pattern that may include directing power to all igniters 32 in the array simultaneously, or in a pattern in which one or more igniters 32 in the array are powered in a timed sequence.

3. Structural Layer

The structural layer 34 is a flat plate structure that provides a rigid structural member for the miniature device 20 and contains at least one holes that define the side walls of at least one well 42, as shown in FIG. 2. The structural layer 34 is constructed with a material ranging in thickness between about 0.5 mm and about 1.5 mm, and with sides ranging between about 10 mm and about 50 mm in length. Any length of side may be used, so long as the resulting structural layer 34 is sufficiently smaller than the substrate 22 in size so that the connection pads 35 of the igniter 32 are left exposed after the structural layer 34 is bonded to the substrate 22, as shown in FIG. 1.

The structural layer 34 may be constructed from materials including but not limited to glass, polycarbonate thermoplastic, stainless steel, silicon, and acrylic. The substrate may be fabricated from another comparably strong and rigid material, so long as the material may receive and hold other members, is resistant to high temperatures, and is not reactive with the energetic material 44.

i. Well

At least one well 42 in the structural layer 42 provides a volume in which to contain the amount of energetic material 44 used to supply the energy for the shock waves generated by the miniature device 20. The wells 42 formed in the structural layer 34 run completely through the thickness of the structural layer 34 and each well 42 has a volume ranging between about 0.1 mm3 and about 6 mm3. The cross-sectional shape of the wells 42 may be any shape, including square, as shown in FIG. 2, or round. The wells 42 may be formed in the structural layer 34 using any method known in the art, including microdrilling, laser machining, acid or chemical etching and hot embossing.

The structural layer 34 may contain between one and about twenty wells 42. The at least one well 42 in the structural layer 34 is positioned directly over the at least one igniter 32 in the assembled miniature device 20.

In an embodiment, the at least one well 42 may be formed in the upper surface 30 of the substrate 22, and the structural layer 34 may be omitted from the miniature device 20. The at least one well 42 in this embodiment does not penetrate completely through the substrate 22, which forms the sides and bottom of the at least one well 42. The at least one well 42 may be formed directly in the upper surface 30 using known techniques including microdrilling, laser machining, acid or chemical etching and hot embossing. The flexible membrane 36 is bonded directly to the upper surface 30 of the substrate 22 in this embodiment.

ii. Exhaust Channels

The exhaust channels 46 are channels connecting the wells 42 to the atmosphere, and act as a vent for the pressurized by-products of the combustion of the energetic material 44 in the well 42. Referring to FIG. 2, the structural layer may contain one or more exhaust channels 46 radiating out from the wells 42 to the outer edges of the structural layer 34, in an embodiment. The one or more exhaust channels 46 acoustically connect the interior of the well 42 to the external atmosphere. The one or more exhaust channels 46 are fabricated on the upper surface 35 of the structural layer 34 using known techniques including mechanical etching, acid or chemical etching, and hot embossing.

During the operation of the miniature device 20, the exhaust channels 46 divert the byproducts of the ignition of the energetic material 44 away from the tubular member 38 and other structures above the flexible membrane 36 of the miniature device 20. Although the exhaust channels 46 controllably release the gas pressure resulting from the ignition of the energetic material 44 in the well 42 during operation of the miniature device 20 in an embodiment, the miniature device 20 may be constructed without any exhaust channels 46.

4. Energetic Material

The shock waves are generated using the energy liberated by the rapid ignition of an energetic material 44. The energetic material may be any combustible compound that produces a combustion front that has a propagation velocity greater than the speed of sound through the surrounding materials. Because of the high rate of combustion, the pressure waves produced by the ignition of the energetic materials 44 are shock waves, characterized by high peak pressures and rapid pressure rise times. The energetic material may be an explosive material, a nanoenergetic material, or a combination thereof. Any energetic material 44 can be used so long as it is stable at room temperatures, and is capable of being ignited by the igniter 32.

The explosive material may be selected from the group including nitrocellulose, glycidyl azide polymer, bisazidomethyloxetane polymer, azidomethyl methyloxetane polymer, silver azide, lead azide, and combinations thereof.

Nanoenergetic materials, previously described in US Patent Application 2007/0095445 and incorporated by reference in its entirety herein, include a mixtures that includes a plurality of metal fuel nanoparticles and a plurality of metal oxide nanoparticles in a crystalline nanostructure that maximizes the contact area between the two reactants, and reacts rapidly and exothermally when ignited. The fuel of the nanoenergetic material has a free energy of oxidation that is lower than the free energy of oxidation of the oxidizer, and thus reacts exothermically when combined with the oxidizer in the presence of activation energy.

In an embodiment, the fuel used in the nanoenergetic material is at least one metal from the list comprising aluminum, boron, beryllium, hafnium, lanthanum, lithium, magnesium, neodymium, silicon, tantalum, thorium, titanium, yttrium and zirconium. In addition, the metal oxide used in the nanoenergetic material is at least one from the list comprising copper oxide, silver oxide, boron oxide, bismuth oxide, cobalt oxide, chromium oxide, iron oxide, mercuric oxide, iodine oxide, manganese oxide, molybdenum oxide, niobium oxide, nickel oxide, lead oxide, palladium oxide, silicone oxide, tin oxide, tantalum oxide, titanium dioxide, uranium oxide, vanadium oxide, tungsten oxide, and combinations thereof. Molecular linkers may be used to bond the fuel and metal oxide together and may be selected from the list comprising of poly(vinyl pyridine), poly(methylmethacrylate), poly(vinyl butyral), poly(vinyl chloride), polycarbonate, polystyrene, fluoropolymers, Teflon, cerboxyterminated butadiene acrylonitrile, glycidal azide polymer, poly(vinyl pyrrolidone), and combinations thereof. In a preferred embodiment, the nanoenergetic material is comprised of bismuth oxide and aluminum nanoparticles.

In another embodiment, the nanoenergetic material may contain one or more additional particles that may be nanoparticles, or particles of a larger size, to increase the energy released from the ignition of the nanoenergetic material. The nanoparticles are selected from the group comprised of propellant and explosive nanoparticles, which are selected from the group including ammonium nitrate, ammonium perchlorate, cellulose nitrate, RDX, TNT, HMX, PBX, CL-20 and combinations thereof.

5. Flexible Membrane

The flexible membrane 36 covers the energetic material 44 inside the wells 42, and transfers the compressive forces released by the ignition of the energetic material 44 to other transmissive elements such as the gel 40 inside of the tubular member 38, or the fluid of a cell suspension. In addition, the flexible membrane 36 prevents the reaction products from the combustion of the energetic material 44 from escaping into the surrounding material and contaminating the tissues or cells being treated. Referring to FIG. 2, the flexible membrane 36 is bonded to the upper surface 35 of the structural layer 34 and forms an upper cover for the wells 42 in the structural layer 34.

The flexible membrane 36 may be fabricated from any viscoelastic material capable of forming into thin layers and adhering to other device 20 components, and possessing sufficient strength to contain the reaction products of the combustion of the energetic material 44. In addition, the material of the flexible membrane 36 should have a density ranging between about 0.8 and about 1.2 g/cm$^3$, to match the density of the biological targets of the device 20, thereby minimizing transmissive losses of the shock waves.

In an embodiment, the flexible membrane 36 is fabricated using polydimethylsiloxane (PDMS), a viscoelastic material that may be formed into layers between about 0.01 mm and about 5 mm thick. The flexible membrane 36 is prepared by mixing pre-polymer and a curing agent and curing the PDMS material in a flat mold. The relative amounts of pre-polymer and curing agent may be varied to control the strength and viscoelastic material properties of the resulting flexible membrane 36 to fall within predetermined limits. The flexible membrane 36, due to its low mass and density near that of the biological target, efficiently transmits the pressure forces generated by the ignition of the energetic material 44, and prevents the reactants of the ignition from escaping and possibly contaminating the transfected cells or tissues.

6. Tubular Member

The tubular member 38 is contacted at one end with the flexible membrane 36 opposite the at least one wells 42 and defines an interior volume that is filled with a gel 40. The tubular member 38 holds the gel 40 in position such that the pressure waves generated beneath the flexible membrane 36 may be transmitted through the gel 40 to the cell samples or tissues. The walls of the tubular member 38 form a cavity with an inside diameter ranging between about 1 mm and about 10 mm, and a length ranging between about 1 mm and about 100 mm. The tubular member 38 may be fabricated from materials including polycarbonate thermoplastic such as Lexan, metals such as stainless steel, acrylic or any other suitably rigid material.

7. Gel

The gel 40 acts as a transmissive medium to conduct the shock waves generated at the flexible membrane 36 to the cells or tissues to be treated. The interior cavity of the tubular member 38 is filled with the gel 40 that efficiently transmits pressure waves to the desired location as well as trapping stray reaction products from the ignition of the energetic material 44, preventing contamination of the cells or tissues in the event of the rupture of the flexible membrane 36. The gel 40 is selected to substantially match the density of the tissues or cells to be exposed to shock waves generated by the miniature device 20, thereby preventing transmissive energy losses. The gel 40 should have a density ranging between about 0.8 and about 1.2 g/cm$^3$. The gel 40 may be selected from the group including Type A gelatins, Type B gelatins, hydrogels, and combinations thereof, whereby the gel 40 has a gel strength ranging between about 50 and about 350 on a Bloom scale.

B. Other Embodiments of Miniature Devices

The miniature device 20 has at least several alternative embodiments depending on the desired application of shock waves to biological cells and tissues.

1. Types and Uses of Miniature Devices

The miniature device 20 may be constructed as a laboratory bench-top device for in vitro applications to cell suspensions or tissue samples, as shown in FIG. 5. The miniature device 20 is held in contact with opening of a container 50 containing a suspension of biological cells 52 and the compound 54 to be transfected into the cells 52. Alternatively, the miniature device 20 may be constructed as an external device to direct shock waves through the epidermis of a living organism, or as a catheter-mounted device to direct shock waves to the internal cells or tissues of living organisms (devices not shown).

The miniature device 20 may be used for a variety of biomedical applications including but not limited to: cell membrane permeabilization, epidermal poration, transdermal delivery of therapeutic compounds, cell transfection, gene therapy, tissue ligation, and the extracorporeal shock wave lithotripsy of kidney stones.

1. Arrays of Miniature Devices

In an embodiment, arrays of miniature devices 20 may be fabricated on a flat or concave surface and ignited in a sequence selected from the group including simultaneous ignition, sequential ignition or a combination thereof to produce shock waves with predetermined properties. Using a combination of arrays of miniature devices 20 and ignition sequences, shock waves with a variety of profiles may be produced. In an embodiment, a linear array of miniature devices 20 fabricated on a flat surface and simultaneously ignited produces a planar shock wave through the constructive interference of the individual shock waves produced by each miniature device 20 in the array. In an embodiment, an array of miniature devices 20 fabricated on a curved surface and ignited sequentially produces a spatially focused pressure wave with a temporally cyclic pressure wave profile.

2. Adjustment of Shock Wave Characteristics

Many of the elements of the miniature device 20 may be adjusted to alter the characteristics of the shock waves such as peak pressure, pressure rise time, pressure wave duration or pressure impulse, shown in FIG. 6. Table 1 summarizes exemplary adjustments to elements of the miniature device 20, and the effects of these adjustments on the pressure profile delivered to the desired location, estimated based on the experimental results described in the Examples below. Other adjustments to the miniature device may include the composition and thickness of the flexible membrane 36, the composition of the gel 40 inside of inner cavity of the tubular member 38.

TABLE 1

Effects of Varying Exemplary Elements of the Miniature Device on the Resulting Shock Wave Profiles.

| | | Effect on Shock Wave Profile Delivered to Tissue | | |
|---|---|---|---|---|
| Element of Device | Adjustment | Pressure onset rate | Peak pressure | Duration of shock wave |
| Amount of energetic material | Increase | no change | increase | increase |
| Composition of nanoenergetic material: fuel/oxide mix | $MoO_3$/Al | baseline | baseline | baseline |
| | $Fe_2O_3$/Al | decrease | increase | increase |
| | CuO/Al | increase | increase | decrease |
| | $Bi_2O_3$/Al | decrease | increase | increase |

TABLE 1-continued

Effects of Varying Exemplary Elements of the Miniature Device on the Resulting Shock Wave Profiles.

| Element of Device | Adjustment | Effect on Shock Wave Profile Delivered to Tissue | | |
|---|---|---|---|---|
| | | Pressure onset rate | Peak pressure | Duration of shock wave |
| Composition of nanoenergetic material: add propellant or explosive nanoparticles | add Teflon | decrease | increase | increase |
| | add Ammonium nitrate | increase | increase | little effect |
| | add RDX | increase | increase | increase |
| Compress energetic material into pellets | increase compression pressure | decrease | decrease | increase |
| Gel-filled tube | remove tube | no change | no change | no change |
| Distance from tissue | increase distance | decrease | decrease | no change |
| Direct shock waves into closed container | decrease size of container | no change | increase* | increase* |

*The closed container captured compression wave from expansion of combustion products as well as shock wave An embodiment that adjusts the profile of the pressure wave delivered to the desired location may vary at least one of the elements described above, or the embodiments may vary combinations of the elements described above.

C. Delivering Compounds to Biological Tissue

The present invention may be used to deliver compounds to biological cells and tissues. A miniature device 20 that includes a substrate 22, at least one igniter 32 in contact with an amount of energetic material 44 and a transmissive barrier 35 placed over the energetic material 44 is provided. The compound is placed in close proximity to the biological target, and a shock wave is generated by igniting the energetic material 44. The shock wave is directed toward the biological target.

The miniature device 20 delivers shock waves to the cells and tissues of bacteria, plants, animals, and fungi with predetermined shock wave profiles that are suitable for delivering compounds to individual cell types without adversely affecting subsequent cell viability or survival. The ability to control the characteristics of the shock waves allows the miniature device 20 to be adapted for use in a wide range of applications. The miniature devices 20 may be used for various purposes in the biomedical field such as cell permeabilization, acceleration of microparticles or nanoparticles, and cavitation. These processes are used for targeted delivery of imaging agents, drugs, or genes, for the ligation of tissues, and for the disintegration of kidney stones.

The compounds to be delivered to the cells or tissues may be placed in close proximity to the cells or tissues, or the compounds may be placed in the gel 40 inside of the cavity formed by the tubular member 38. Compounds to be delivered may be placed in close proximity to the cells or tissues using methods selected from the group including oral ingestion, topical application, inhalation, rectal suppository application, implantation, and injection.

The design features make it possible for the miniature device 20 to transfect cells with a variety of substances such as plasmids, gold nanoparticles, and silica nanospheres or nanoparticles of other shapes containing rhodamine or other dyes. The transfected cells may vary based on diverse morphological properties. For example, embryonic cardiomyocytes are notoriously resistant to transfection by any means, and spinal cord cells are known to be very fragile to physical transfection methods. A high degree of transfection efficiency occurs when using the miniature device 20 without compromising cell survivability or post-transfection cell function.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

EXAMPLES

The following examples illustrate the invention.

Example 1

Sensitivity of Shock Wave Characteristics to the Composition of the Nanoenergetic Material was Demonstrated in the Experimental Device A device was tested to determine whether it was capable of manipulating the characteristics of a shock wave. Such characteristics include pressure rise-time, the duration of the shock wave, the peak pressure (intensity) of the shock wave, and the net impulse produced by the shock wave. To assess the effects of the composition of the nanoenergetic materials on the characteristics of the shock wave produced by the present invention, a study was conducted using an experimental shock wave generating apparatus.

Figure 7:
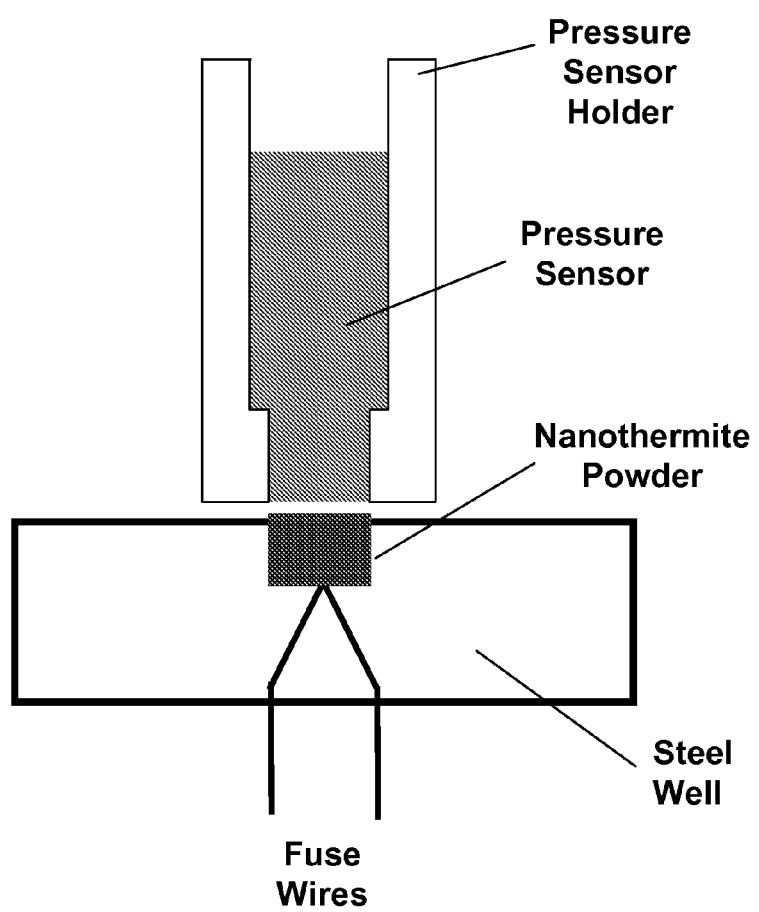
FIG. 7 is a drawing of the experimental device used for measuring the pressurization rates of nanoenergetic materials.

The device used in this experiment, shown in FIG. 7, consisted of a steel plate with a circular well to hold the nanoenergetic material, an igniter, and a pressure sensor mounted just above the well in the steel plate. The well had a diameter of 6.25 mm and a depth of 2 mm, resulting in a total well volume of 61.35 mm$^3$. The pressure sensor was a piezoelectric pressure sensor (PCB Piezotronics Model 119B12) with maximum pressure range of 827 MPa. Ignition of the nanoenergetic material was triggered by a Ni-alloy fuse wire with a diameter of 0.13 mm (Parr P/N 45C10), clamped inside the well.

To conduct the experimental measurement of shock wave characteristics, 20 mg of nanoenergetic material was packed into the well, the fuse wire and pressure sensor were clamped into place, and the nanoenergetic material was ignited. Signal from the pressure sensor was applied to a charge sensitive inline preamplifier and signal conditioner (PCB Piezotronics Mod. #482A22). A four channel digital oscilloscope (Tektronix TDS3014B, 100 MHz bandwidth) recorded the analog signal from the pressure signal conditioner. Each nanoenergetic material was tested in the experimental apparatus at least 3 times.

Figure 6:
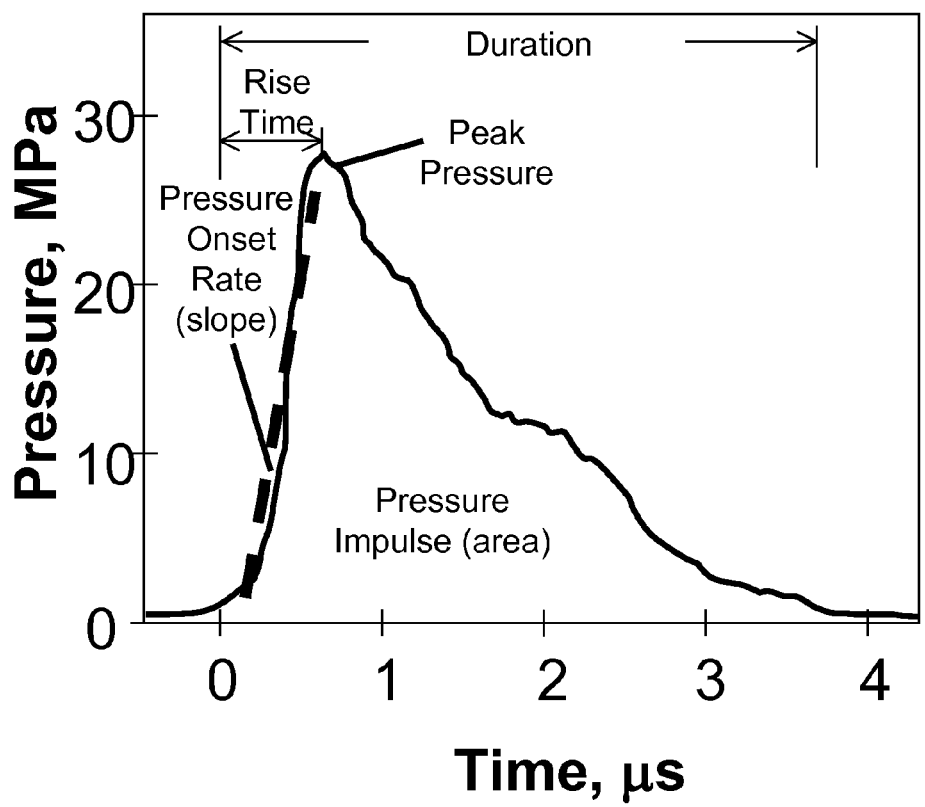
FIG. 6 is an illustration of an exemplary shock wave profile, showing rise time, pressure onset rate, peak pressure, and pressure impulse generated by the ignition of nanoenergetic material.

Rise-time, pressurization rate, and peak pressure of the recorded pulses were assessed using the pressure measurements. The measured pressures were analyzed to determine the maximum (peak pressure), and the pressurization rate was calculated by finding the slope of the rising edge of the pulse (from 10% to 90% of the peak pressure). A typical pressure measurement record is shown in FIG. 6, and the peak pressure ($P_{max}$), pressure onset time, and pressurization rate are identified with labels.

Figure 8:
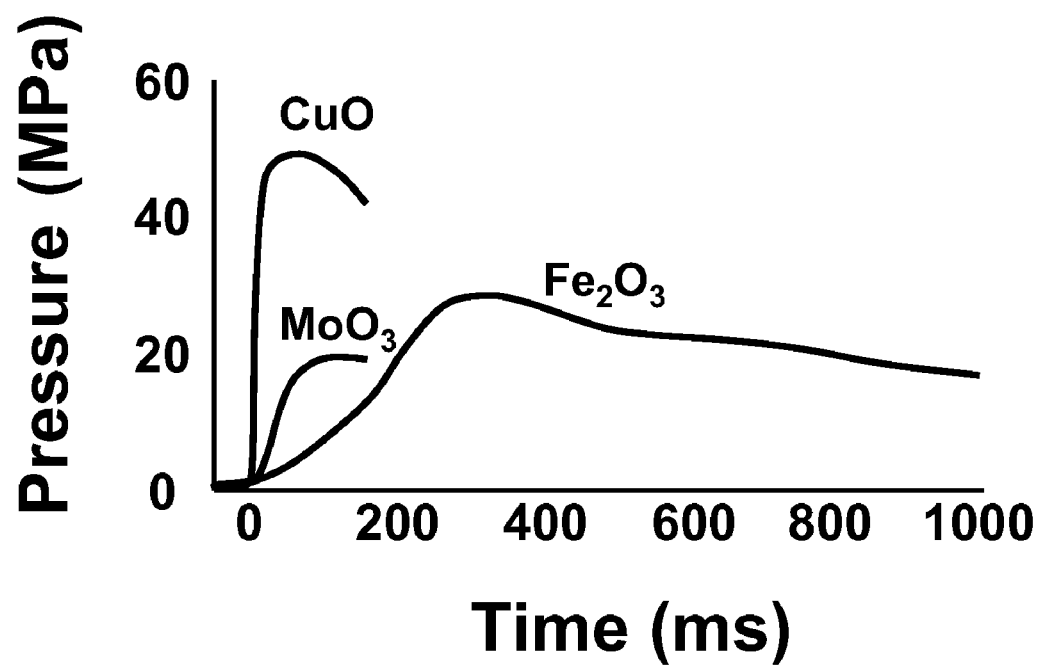
FIG. 8 is a graph of pressure wave profiles showing the effect of the nanoenergetic material composition on the resulting shock wave characteristics.

Nanoenergetic fuel/oxidizer formulations with 80 nm Aluminum nanoparticles (Al80) and three different oxidizer nanorods ($CuO$, $Fe_2O_3$, and $MoO_3$) were tested. An optimal equivalence ratio of 1.6 (i.e., a fuel-rich mixture) was used in each experiment. Nanoenergetic material in powder form (20 mg) was packed into the well of the experimental apparatus, ignited, and the resulting shock wave was measured and analyzed. A comparison of the typical shockwave characteristics for the three formulations tested is shown in FIG. 8. The CuO/Al formulation yielded the highest peak pressure and pressure onset rate, with the shortest duration. The $Fe_2O_3$/Al formulation had the slowest pressure onset rate, an intermediate peak pressure, and the longest duration of the pressure wave compared to the other two formulations. The $MoO_3$ formulation had an intermediate pressure onset rate and lowest peak pressure, and pressure wave duration of similar magnitude to the CuO/Al formulation. Based on the significantly higher peak pressure measured relative to the other formulations, the CuO/Al formulation was determined to be the most promising formulation for use in biomedical applications.

The results of these experiments demonstrated that the reactivity of the nanoenergetic material was very sensitive to changes in the oxidizer material. Manipulation of the composition of the nanoenergetic material was a highly effective means of fine-tuning the characteristics of the shock wave generated by the device to desired levels. Based on previous studies, pressure waves with short rise times, high peak pressures, and long shock wave durations are considered to be the most effective for cell transfection (Doukas and Kollias, 2004). The CuO/Al composition was selected as the preferred nanoenergetic material composition due to shock wave characteristics that included the highest peak pressures and fastest onset times of any of the fuel/oxide compositions tested.

Example 2

Figure 9:
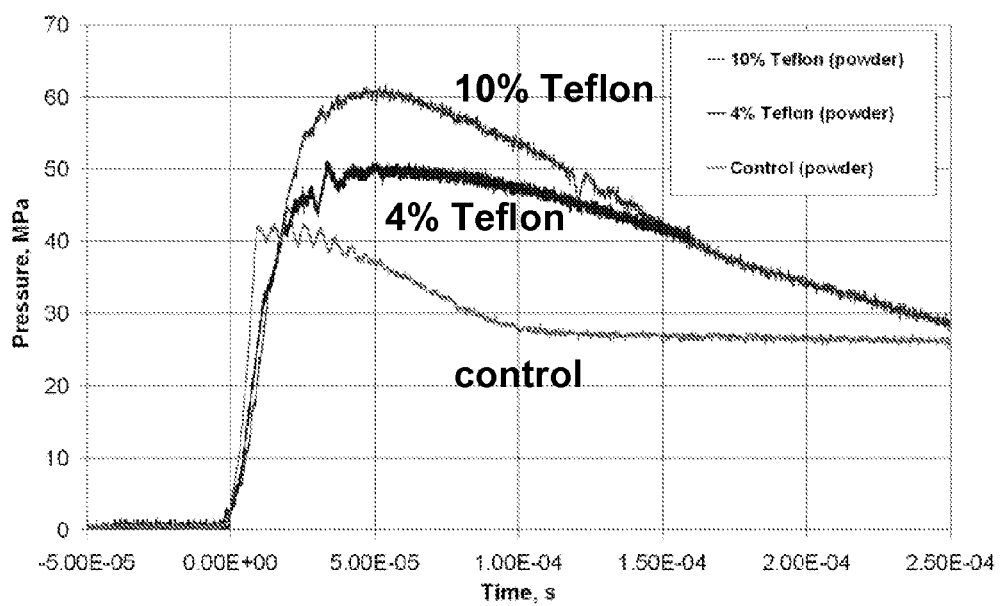
FIG. 9 is a graph of pressure wave profiles showing the effect of the addition of powdered Teflon to the CuO/Al nanoenergetic material composition on the resulting shock wave characteristics.
Figure 10:
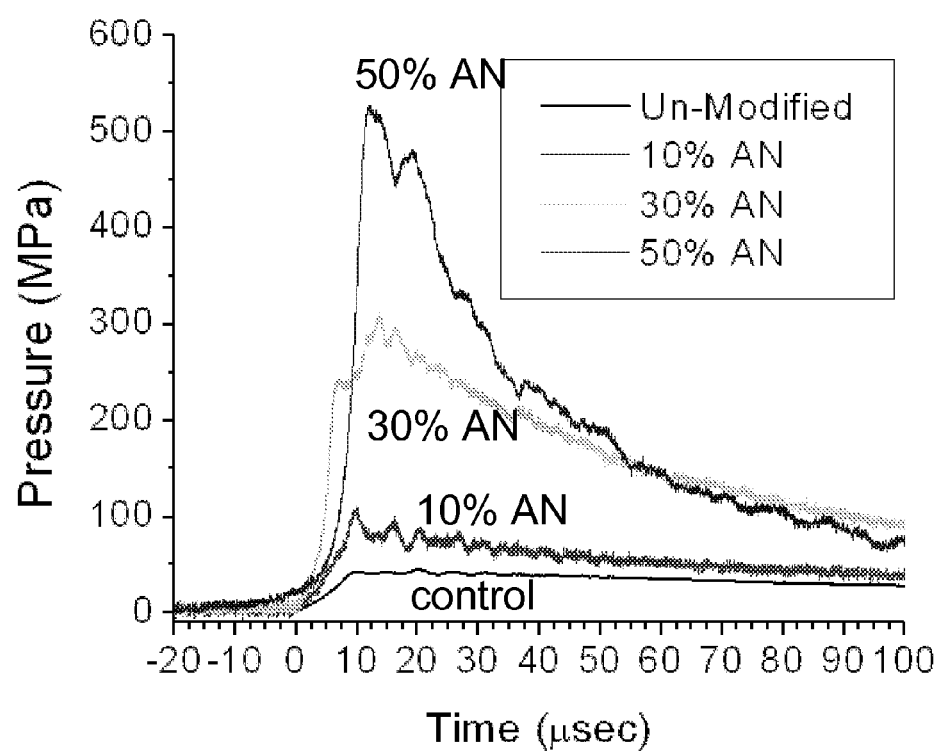
FIG. 10 is a graph of pressure wave profiles showing the effect of the addition of ammonium nitrate (AN) to the CuO/Al nanoenergetic material composition on the resulting shock wave characteristics.
Figure 11:
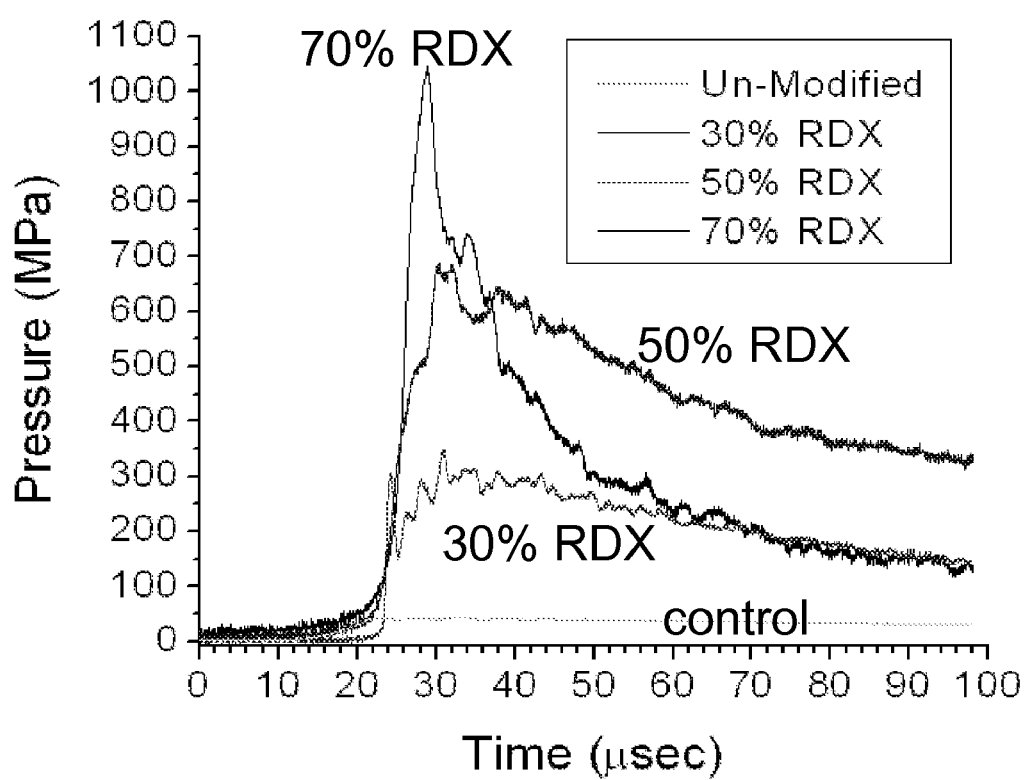
FIG. 11 is a graph of pressure wave profiles showing the effect of the addition of cyclotrimethylenetrinitramine (RDX) to the CuO/Al nanoenergetic material composition on the resulting shock wave characteristics.

Sensitivity of Shock Wave Characteristics to Additives to the Nanoenergetic Material was Demonstrated in the Experimental Device Using the experimental methods and device described in Example 1, the nanoenergetic material formulation with 80 nm aluminum nanoparticles and CuO oxidizer was tested with the addition of three different high explosive nanoparticles: Teflon (T), Ammonium Nitrate (AN), and RDX particles. 20 mg samples of the nanoenergetic materials in powder form with the additives were tested in a similar manner to previous experiments. The AN and RDX used were in the form of nanoparticles or in a larger size. The pure CuO/Al formulation was compared to CuO/Al with 4% and 10% powdered Teflon added, CuO/Al with 10%, 30% and 50% ammonium nitrate added, and CuO/Al with 30%, 50%, and 70% RDX added. An optimal equivalence ratio of 1.6 (i.e., a fuel-rich mixture) was used in each experiment. FIG. 9, FIG. 10 and FIG. 11 show a comparison of the measured pressure waves resulting from the ignition of the various formulations described above. The addition of Teflon powder to the CuO/Al nanomaterial (FIG. 9) resulted in a modest increase in peak pressure, and a modest increase in the pressure impulse (area under the pressure curve). The addition of ammonium nitrate (FIG. 10) resulted in a peak pressure that was up to 10 times larger than the nanoenergetic material with no additives. The addition of RDX to the CuO/Al nanomaterial (FIG. 11) resulted in a peak pressure up to 20 times larger than the nanoenergetic material with no additives. Although the duration and onset times of the pressure waves were essentially unchanged by any of the additives, the pressure impulses and pressure onset rates were significantly increased as a result of the additives, due to the sizable increases in the peak pressures during the pressure waves.

The results of this experiment demonstrated that the peak pressure may be readily manipulated through the inclusion of high explosive nanoparticles to the nanoenergetic materials. The addition of Teflon powder to the nanoenergetic material caused the intensity of the pressure wave to increase with little effect on the rise time. The addition of ammonium nitrate or RDX increased the intensity of the pressure wave, with little effect on the rise-time. Although the addition of RDX yielded the highest increase in shock wave intensity, exposure to shock wave energy of this intensity would most likely result in cell or tissue damage. Ammonium nitrate, which also yielded significantly increased, but more moderate, shock wave intensity relative to RDX, was selected as the preferred additive to the nanoenergetic material in subsequent studies.

Example 3

Figure 12:
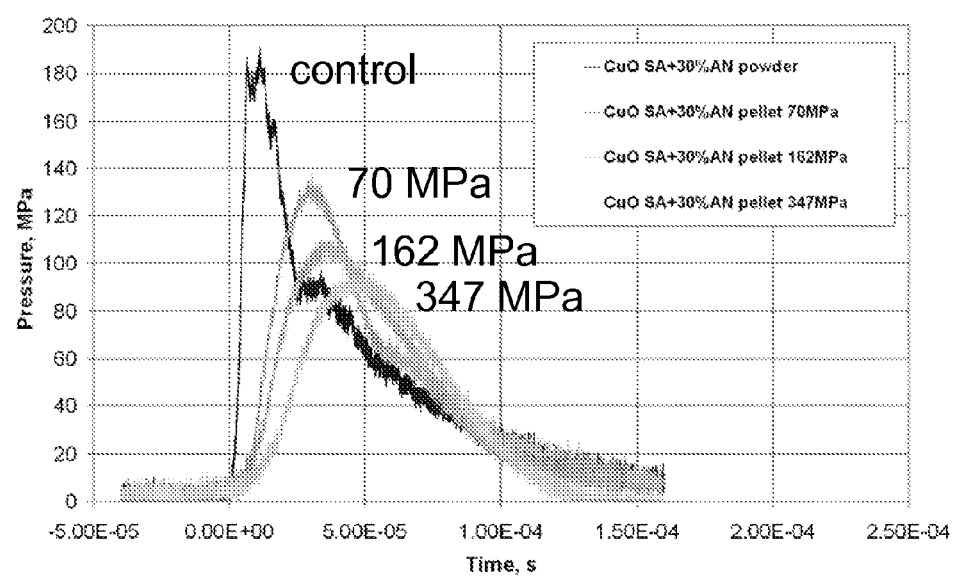
FIG. 12 is a graph of pressure wave profiles showing the effect of compressing CuO/Al/AN nanoenergetic material into pellets using different pressures on the resulting shock wave characteristics.

Sensitivity of Shock Wave Characteristics to the Packing of Nanoenergetic Material into Pellet Form was Demonstrated in the Experimental Device Using the experimental methods and device described in Example 1, the nanoenergetic material composed of CuO nanorods, aluminum nanoparticles, and 30% ammonium nitrate was tested to determine the effect of pressing the nanoenergetic material into pellets of different densities. Twenty milligrams of nanoenergetic material in powder form was loaded into a steel die and pressed into pellets with an outer diameter of 4.8 mm by a hand hydraulic press at pressures of 70, 162, and 347 MPa. The pellets were loaded into the experimental apparatus and tested in a similar manner to the powder sample in previous experiments. An optimal equivalence ratio of 1.6 (i.e., a fuel-rich mixture) was used in each experiment. The results of pressure and reactivity measurements for the pellets formed using the three different packing pressures are compared to a measurement taken from the ignition of a 20 mg powder sample in FIG. 12. The compression of the CuO/Al nanoenergetic material into pellets resulted in a pressure onset time up to five times longer than the powder form, a significantly decreased pressure onset rate, and a peak pressure as low as 50% of the peak pressure measured from the ignition of the powdered form of the nanoenergetic material.

The results of these experiments demonstrated that compressing the nanoenergetic material into pellet form was another means of controlling the reactivity of nanoenergetic materials, and by extension the shock wave characteristics resulting from their ignition. Increasing the packing density of the nanoenergetic material reduces the intensity and lengthens the rise time and duration of the pressure wave. Although the powdered form of the nanoenergetic material remained the preferred embodiment for subsequent studies, the compression of the nanoenergetic material into pellet form was identified as an effective means of reducing the shock wave intensity and rise time if deemed necessary in future applications of the device.

Example 4

Figure 13:
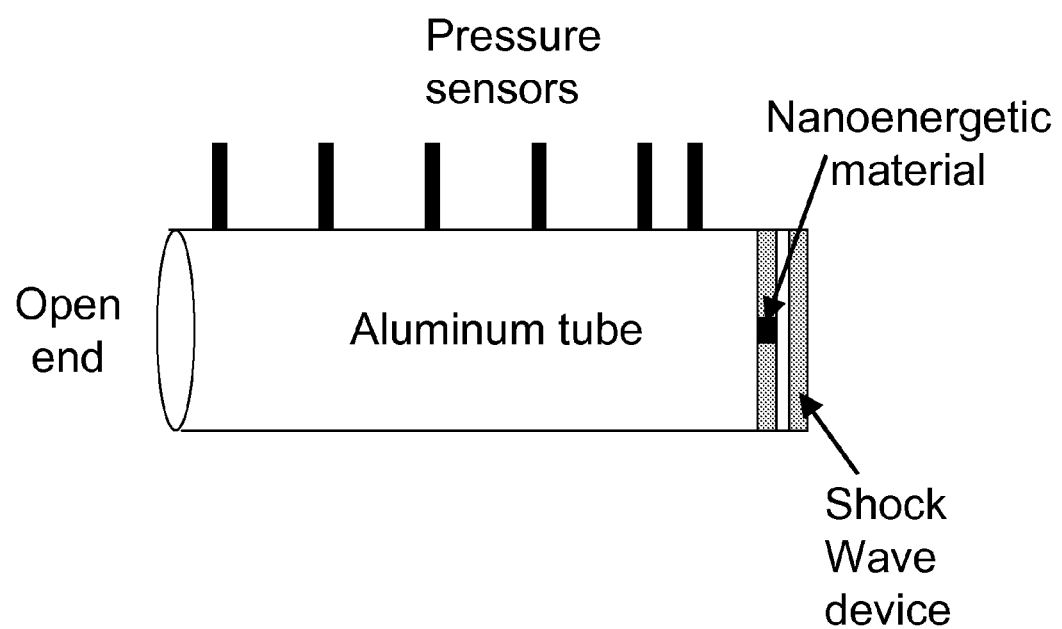
FIG. 13 is a side view drawing of the compact air-filled shock tube system used to measure the propagation velocity of shock waves.

The Supersonic Propagation Speed of Shock Waves Generated by the Ignition of Nanoenergetic Materials was Sensitive to the Quantity and Composition of the Nanoenergetic Material To assess the propagation rate of the pressure waves produced by an experimental shock wave generator, shock waves were measured by a compact air-filled shock tube system, illustrated in FIG. 13. The shock wave generator was clamped against the end of the shock tube such that the shock wave propagated directly from the device into the tube. Pressure transducers mounted along the length of the tube recorded pressure time-histories and measured the shock wave's intensity, propagation rate, and acceleration.

An experimental shock wave generation device similar to that described in Example 1 was used to measure the effects of the nanoenergetic material composition on the propagation speed of the shock waves. The devices were loaded with a physical mixture of CuO nanorods and Al nanospheres ranging in mass from 0.1 mg to 20 mg, mounted in the compact shock tube, and the pressure waves resulting from ignition were measured. For this range of masses of nanoenergetic materials, the shock waves varied in velocity from Mach numbers of 1.1 to 2.49. When ammonium nitrate nanoparticles were added to 10 g of the CuO/Al composition in an amount ranging up to 30% by weight of ammonium nitrate nanoparticles, the shock wave velocity increased from a Mach number of 2.05 to 3.20. Changing the quantity of material and modifying (doping) the nanoenergetic material manipulated the velocity of the shock waves produced by the shock wave generation device. Although this observation provided insight into the physical mechanisms governing the generation of shock waves by the device, it remained to be determined whether the wave propagation speed of shock waves was a significant factor in the transfection of cells by shock waves.

Example 5

Shock Wave Transfection of Living Cells and Tissues was Demonstrated Using Prototype Device The effectiveness of the proposed invention for transfecting living cells was demonstrated using a prototype device on suspensions of chicken cardiac cells (cardiomyocytes), dorsal root ganglion and spinal cord cells as well as entire chicken hearts. In the first stage of this study, living cells were exposed to shock waves generated by the prototype device, described above, and their viability was assessed. Further experiments used the prototype shock wave generation device to transfect living cells and tissues, and the effectiveness of the transfection as well as the viability of the transfected cells were assessed.

Chicken cardiac cells were suspended at a cell density of 106 cell/ml in cell culture medium (Neurobasal+B27) in 1.5 ml micro-centrifuge tubes. The suspended cells were exposed to shock waves generated by a prototype device as described above. A 50-μl sample of the cells was drawn before and after shock wave exposure and labeled with 0.4% trypan blue solution. The trypan blue dye did not enter into living cells, whereas the dead cells readily took up the dye. Dye-impregnated dead cells for each sample were counted using a light microscope. 99.3±4% of the cells were properly transfected and 99.1±7% survived the transfection procedure after 24 hrs in culture with no apparent changes in their function or morphology. Transfected cells were incubated for up to 5 days and had a comparably high rate of transfection and survival.

In a second experiment, the prototype device was used to transfect living cells with eGFP (Enhanced Green Fluorescent Protein) to assess the survivability and transfection efficiency of the prototype device. Cell suspensions of chicken cardiac cells mixed with plasmids containing pGFP were exposed to shock waves in a manner similar to that described above. Transfection efficiency and cell viability were assessed by counting cells under a light microscope after transfection and after subsequent periods of incubation. Transfected cardiomyocytes produced stable eGFP after 72 hrs in culture. In addition, chicken hearts at stage 20-30 were also successfully transfected with plasmids containing pEGFP resulting in similarly high transfection efficiencies and survival rates.

Follow-up testing successfully transfected larger nanoparticles into living cells and tissues. Gold nanoparticles and silica nanospheres containing rhodamine dye, both with diameters of approximately 20 nm, were successfully transfected into chick spinal cord, dorsal root ganglion cells (DRGs), intact hearts and suspensions of cardiomyocytes.

These results demonstrated a significant improvement in overall performance of the present invention compared with existing transfection systems. This experiment demonstrated high transfection efficiency and subsequent cell viability using the present invention on embryonic cardiomyocytes, one of the most difficult cell types to transfect by any chemical or physical methodology. Additionally the expressions of the green fluorescent marker for several days in the transfected cardiomyocytes suggest that permanent transfection is possible with the present invention. The successful transfection of the entire heart suggests that our device could be easily used in single cell suspension as well as in an entire tissue, with minimal tissue damage. Because the shock waves generated by the present invention are readily adjustable, it is possible to transfect relatively fragile spinal cord cells and more robust cardiac cells that require considerably stronger shock waves with the same device. Furthermore, the successful transfection of silica nanospheres containing rhodamine dye demonstrates the viability of using the present invention to deliver pharmaceutical compounds into living cells and tissues.

Example 6

Prototype Cell Transfection Device was Tested to Determine the Effect of the Transmission Tube on Shock Wave Profiles In order to evaluate the effects of the amount of nanoenergetic material on the range of shock wave profiles achievable in a prototype cell transfection device, the following experiment was conducted. Nanothermite mixtures were formed by combining $Bi_2O_3$ nanoparticles (Accumet Materials Co.) having a particle size of 90-200 nm and Al nanoparticles (Novacentrix) having an average particle size of 80 nm in addition to an outer 2.2 nm oxide layer. 200 mg of $Bi_2O_3$ nanoparticles were dispersed in 1.5 mL of isopropanol and agitated using ultrasound sonication for 30 minutes. After the $Bi_2O_3$ nanoparticles were dispersed, 46.3 mg of Al nanoparticles were added to the slurry, followed by sonication for an additional 4 hours. The mixture was then dried in a convection oven at 90° C. for 15 minutes to remove all isopropanol. The resulting nanoenergetic powder was used as the propellant in the prototype transfection device described below.

The prototype cell transfection device used in this experiment included a gel-filled transmission tube secured on top of a PDMS membrane, which was in turn bonded over the nanothermite-filled wells of a microchip.

Figure 14:
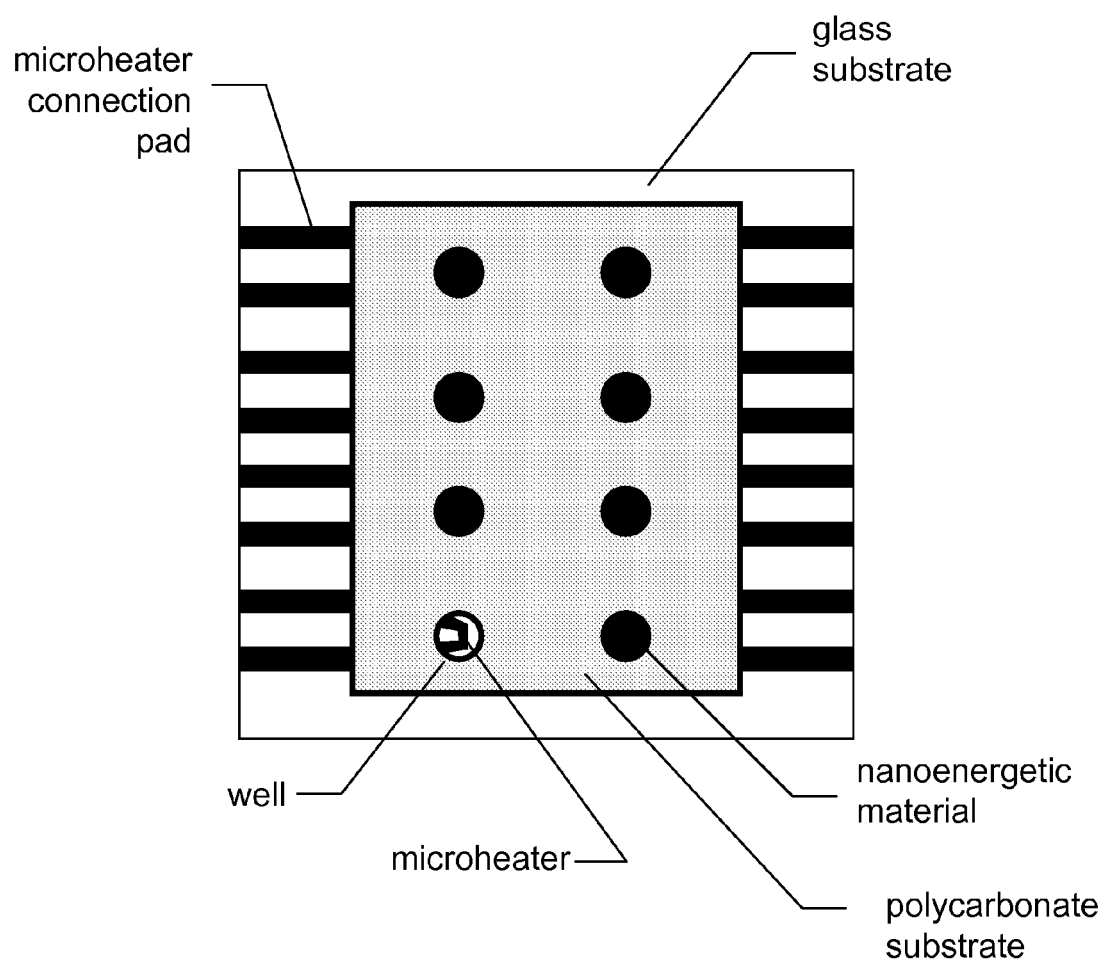
FIG. 14 is a top view drawing of a microchip with igniters and nanoenergetic materials in wells.

The microchips, illustrated in FIG. 14, consisted of six or eight individual wells fabricated in a 25.4×25.4 mm square. The microchips were fabricated using two substrates. Microheaters (one for each well) were fabricated onto a glass substrate using photoresist lift-off patterning, and sputter deposition of Pt/Ti thin films. The wells were fabricated in a polycarbonate substrate by micro-drilling. The polycarbonate substrate was bonded to the glass substrate such that the wells were aligned over the microheaters. Bonding was carried out using low-viscosity adhesive glue. Wires were soldered to the connection pads on the microheaters, and 3 mg of the powdered $Bi_2O_3/Al$ nanothermite material was manually packed into each of the wells. A 1 mm-thick cured PDMS membrane was then placed over the nanoenergetic material-filled wells.

Figure 5:
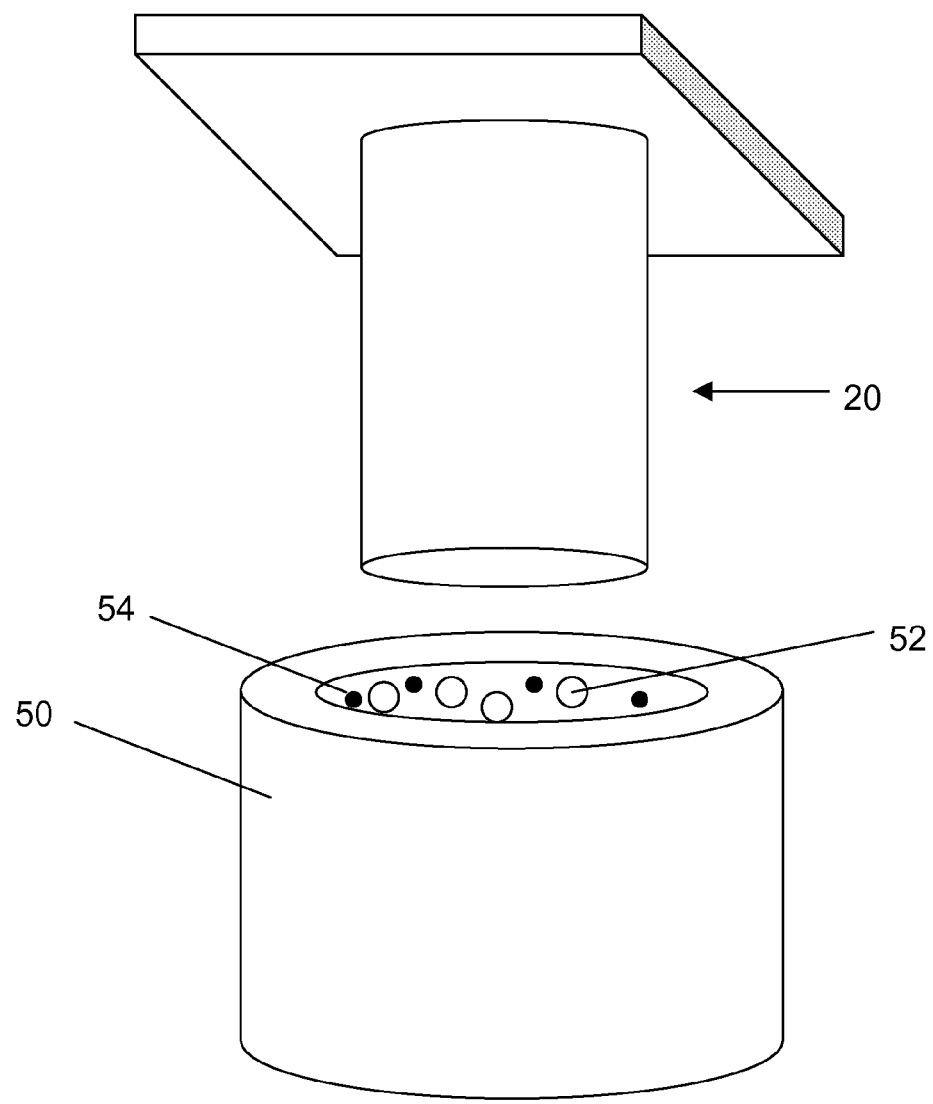
FIG. 5 is an exploded view of an embodiment of a cell transfection apparatus.

The gel-filled transmission tube was fabricated using a stainless steel tube with a length of 25 mm and internal diameter of 3.2 mm. Gelatin was formed from porcine skin and dissolved in water (20% gelatin by weight). The gelatin was heated to 50° C., injected into the steel tube and then cooled to room temperature. A housing was used to hold the gel-filled transmission tube onto the microchip and to align the tube with each nanothermite energy source. FIG. 5 illustrates the assembled elements of the prototype cell transfection device.

A standard 9V battery was used to power the microheaters used to ignite the nanoenergetic material. The nanoenergetic material in each well was ignited individually during the experiments described below, so that one microchip could be used for 6-8 different measurements.

A test bench was used to measure the pressure waves developed by the ignition of the nanoenergetic material in the prototype cell transfection device. The test bench consisted of a small water vessel made from polycarbonate with internal dimensions of 4"×4"×3" (W×L×H), and wall thickness of 0.375". An upwards-facing pressure transducer (PCB 134A02) was mounted in the center of the bottom of the water vessel. The pressure transducer had a 3 mm-diameter tourmaline sensing element, a dynamic range of 137 MPa, a resonant frequency of 1.5 MHz, and a rise time of 0.2 μsec. The vessel was mounted to an optics breadboard with stainless steel rods fixed to the bench.

The prototype cell transfection device was suspended from the stainless steel rods into the water tank facing downwards toward the pressure sensor. A high-speed camera (Photron Fastcam SA1.1) was used to record observable events in the interior of the tank during the ignition of the nanoenergetic material. The microheater in the prototype cell transfection device was synchronized with the pressure sensor data acquisition and high-speed video recording by the same triggering switch.

Figure 15A:
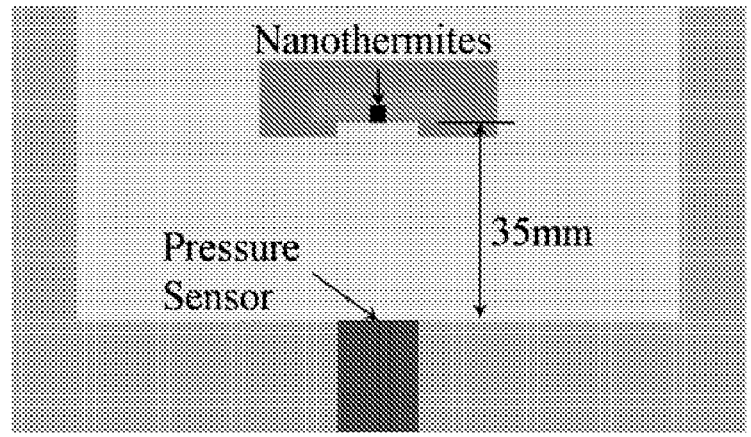
FIG. 15A and FIG. 15B are side view drawings shows the arrangement of the prototype cell transfection devices in the water containers.
Figure 15B:
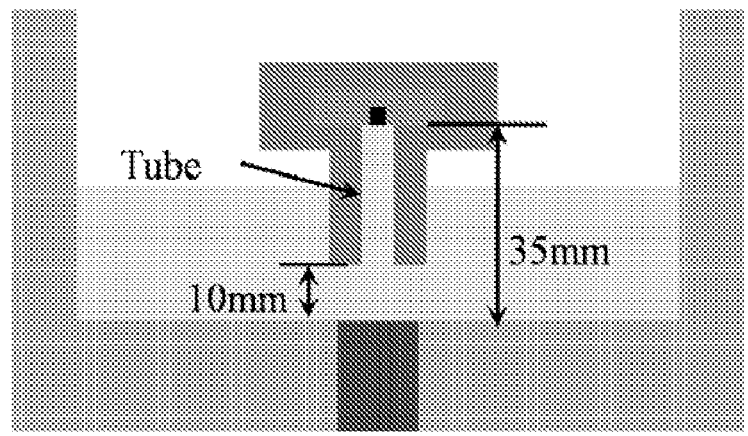

The pressure generated directly from the microchip without the gel-filled transmission tube was measured by sealing the microchip Parafilm, and submerging the microchip in the water vessel, as shown in FIG. 15A. For comparison, the prototype cell transfection device was prepared with the PDMS membrane and the gel-filled tube, and the output through the transmission tube was measured, as shown in FIG. 15B. Both configurations were mounted at a distance of 35 mm from the pressure sensor, and the measured pressure waves generated by the two devices were measured to investigate any changes in pressure-wave attenuation due to the PDMS membrane and gel-filled tube.

Figure 16:
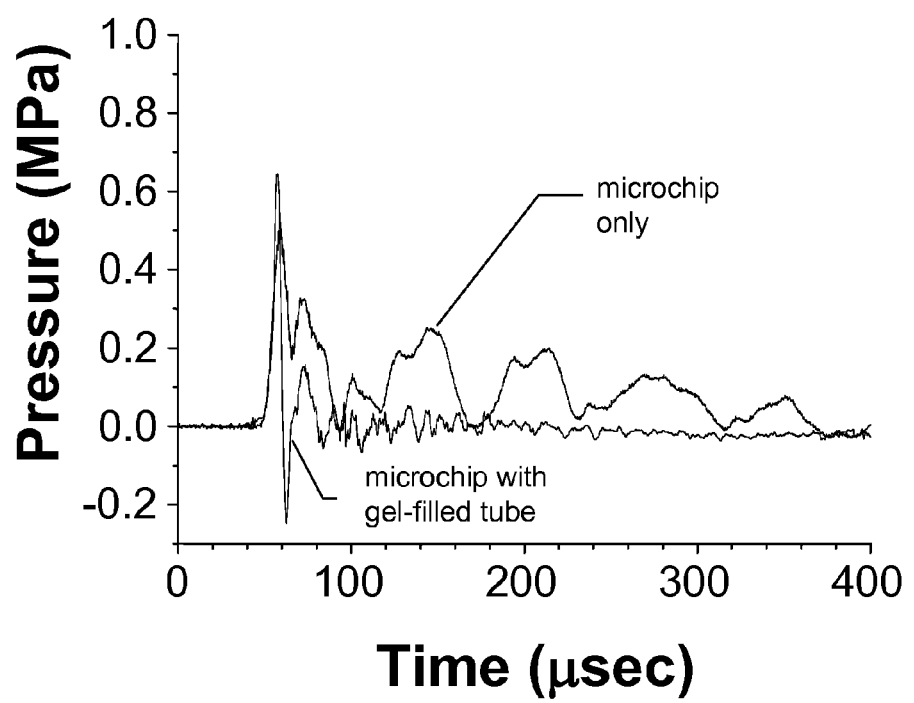
FIG. 16 is a graph showing the effect of the transmission tube on shock wave profiles generated by prototype cell transfection devices.

The pressure measurements for the prototype cell transfection device profiles with and without the transmission tube and PDMS membrane are compared in FIG. 16. The initial pressure rise due to the shock wave generated by the ignition of the nanoenergetic material is transmitted through the transmission tube, with slightly attenuation than when the tube and PDMS are not present. Further, the transmission tube and PDMS membrane filter out the pressure transients induced by the expansion wave that follows behind the shock front, due to the physical containment of the solid and gaseous reaction products by the PDMS membrane.

The results of this experiment determined that the gel-filled transmission tube and PDMS membrane in the prototype cell transfection device did not attenuate the peak pressure of the shock wave produced by the ignition of the nanoenergetic materials. Further, the transmission tube and PDMS membrane greatly attenuated the pressure transients induced by the detonation products resulting from the ignition of the nanoenergetic materials.

Example 7

Prototype Cell Transfection Device was Used to Evaluate the Effect of Nanoenergetic Material Composition on Shock Wave Profiles To determine the sensitivity of the shock wave profiles generated by the prototype cell transfection device to the composition of the nanoenergetic material used to generate the shock waves, the following experiment was conducted.

Prototype cell transfection devices similar to those described in Example 6 were assembled with the following nanoenergetic materials packed into the wells: 3 mg of $Bi_2O_3/Al$ nanothermite material, 15 mg of $Bi_2O_3/Al$ nanothermite material, and 15 mg of nanothermite material comprising 70% $Bi_2O_3/Al$ and 30% ammonium nitrate by weight. The microchips with transmission tubes were mounted with the open end of the transmission tube placed over the opening of a vessel containing water, similar to the apparatus shown in FIG. 5. A pressure transducer (PCB 134A02) was installed in the bottom of the vessel. The nanoenergetic materials were ignited and the resulting shock wave-induced pressures were measured by the pressure transducer.

Figure 17:
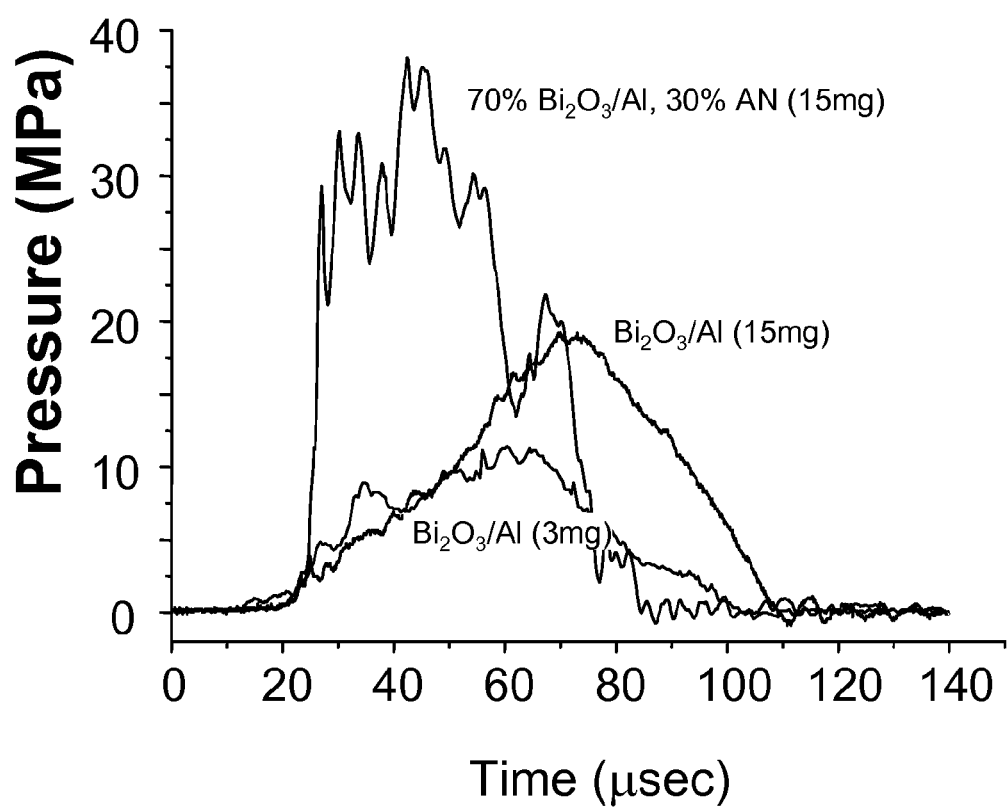
FIG. 17 is a graph showing the effect of varying the amount and composition of nanoenergetic material on the shock wave profiles generated by the prototype cell transfection device.

The results of these measurements are summarized in Table 2. In addition, a graph comparing the pressure profiles corresponding to the ignition of the nanoenergetic materials tested is shown in FIG. 17. Increasing the amount of $Bi_2O_3/Al$ material nearly doubled the peak intensity and pressure impulse generated by the ignition of this composition of nanoenergetic material without significantly changing the duration (FWHM) of the shock wave. In addition, FIG. 18 indicates that the initial rate of pressure increase is approximately the same for both $Bi_2O_3/Al$-generated shock waves, but the rise time is significantly longer for the 15 mg of $Bi_2O_3/Al$ shock wave, due to its higher peak intensity. Because the two $Bi_2O_3/Al$-induced shock waves have similar durations, the time to return to ambient pressure after the peak intensity of the shock wave is significantly shorter for the shock wave induced using 15 g of $Bi_2O_3/Al$ nanoenergetic material. The change in the composition of the nanoenergetic material to a mixture of $Bi_2O_3/Al$ and ammonium nitrate (AN) significantly increased the initial rate of pressure rise, the rise time, the peak intensity, and the pressure impulse relative to a comparable mass of pure $Bi_2O_3/Al$, without significantly affecting the duration of the shock wave.

TABLE 2

Pressure Profile Summary for Three Nanoenergetic Materials.

| Nanoenergetic Material | Quantity (mg) | Peak Intensity (MPa) | Duration (μsec) | Pressure Impulse (Pa-s) |
|---|---|---|---|---|
| $Bi_2O_3/Al$ | 3 mg | 12.94 ± 1.78 | 50.4 ± 4.39 | 584.1 ± 64.2 |
| $Bi_2O_3/Al$ | 15 mg | 21.03 ± 2.44 | 47.2 ± 2.78 | 1002.5 ± 88.6 |
| 70% $Bi_2O_3/Al$ 30% AN | 13 mg | 37.37 ± 3.2 | 41.22 ± 2.23 | 1274.1 ± 70.0 |

The results of this experiment demonstrated that the peak intensity, rise time, initial rate of pressure increase, and total impulse induced by the ignition of nanoenergetic material in a prototype cell transfection device may be independently controlled by alterations in the quantity and/or composition of the nanoenergetic material packed into the wells of the device. However, the results of this experiment did not observe any significant differences in the duration of the shock wave-induced pressure transient between the different configurations of nanoenergetic materials tested.

Example 8

Prototype Cell Transfection Device was Used to Evaluate the Effect of Separation Distance on Shock Wave Profiles To evaluate the spatial distribution of the peak pressures of the shock waves generated by a prototype cell transfection device as a function of separation distance, the following experiment was conducted. Microchips without the transmission tubes were mounted on a test bench similar to the configuration illustrated in FIG. 15A and described in Example 6. In this experiment, the distance separating the microchip from the pressure sensor was varied between 5 mm and 40 mm for different experimental set-ups. In addition, two different compositions of nanoenergetic materials were tested in the microchips: 1.4 mg CuO/Al (described in Example 1), and 3 mg $Bi_2O_3$/Al (described in Example 6). The nanoenergetic materials were ignited and the resulting shock wave-induced pressures were measured using methods similar to those described in Example 6.

Figure 18:
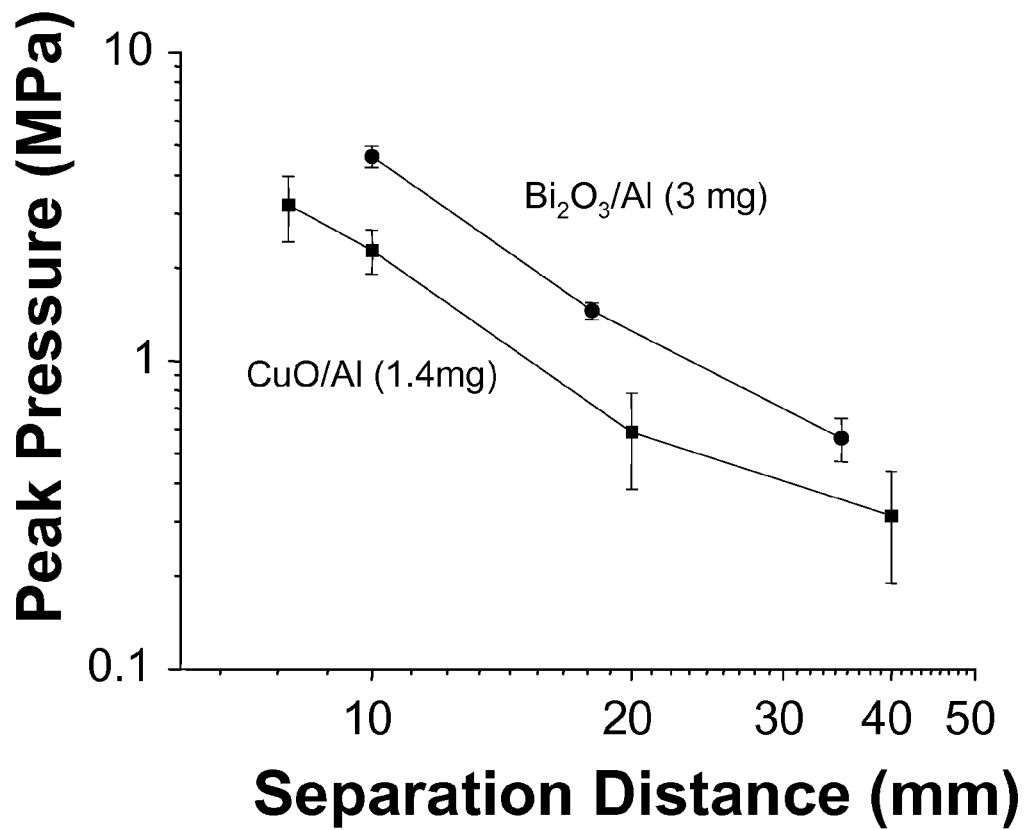
FIG. 18 is a graph showing the effect of separation distance on the peak pressure generated by the prototype cell transfection devices.

The peak pressures measured during this experiment are summarized in FIG. 18. The peak pressures measured for both nanoenergetic material compositions were sensitive to changes in distance. For the $Bi_2O_3$/Al material, a four-fold increase in the separation distance caused a nearly ten-fold decrease in the peak pressure.

The results of this experiment demonstrated that the peak pressures experienced by cells or tissues that are subjected to shock waves from the prototype cell transfection device will be dependent upon the separation distance of the device from the cells or tissues affected. Separation distance is an effective means by which the shock wave characteristics of the prototype cell transfection device may be controlled.

Example 9

Prototype Cell Transfection Device was Used to Evaluate the Effect of Container Volume Diameter on Shock Wave Profiles To evaluate the effect of the volume of the container used for cell transfections using the prototype cell transfection device on the resulting shock wave profiles, the following experiment was conducted.

Figure 19:
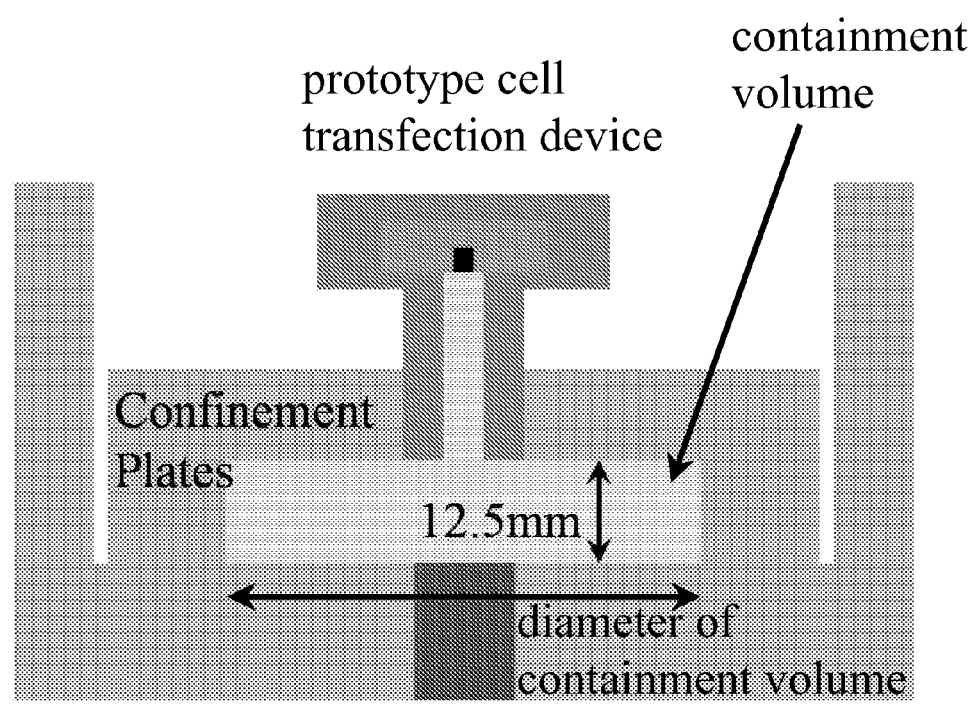
FIG. 19 is a side view drawing of the experimental apparatus used to measure the effect of container diameter on shock wave characteristics.

Prototype cell transfection devices (with transmission tubes) were mounted on a test bench similar to the configuration described in Example 6. In this experiment, the diameter of the water container volume of the test bench was varied between 9 mm and 53 mm, while holding the height of the water container at a constant value of 12.5 mm, as illustrated in FIG. 19. $Bi_2O_3$/Al nanoenergetic material (3 mg) was packed into the wells of the microchip igniters used for all experiments. The nanoenergetic materials were ignited and the resulting shock wave-induced pressures were measured using methods similar to those described in Example 6.

Figure 20A:
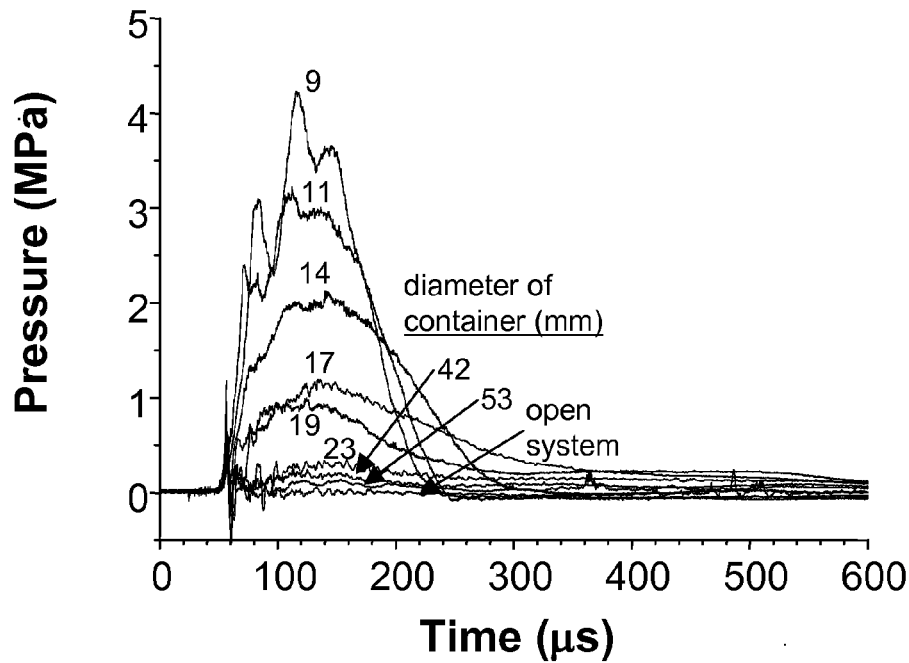
FIG. 20A and FIG. 20B are graphs showing the effect of water container diameter on the pressure profiles generated by the prototype cell transfection devices.
Figure 20B:
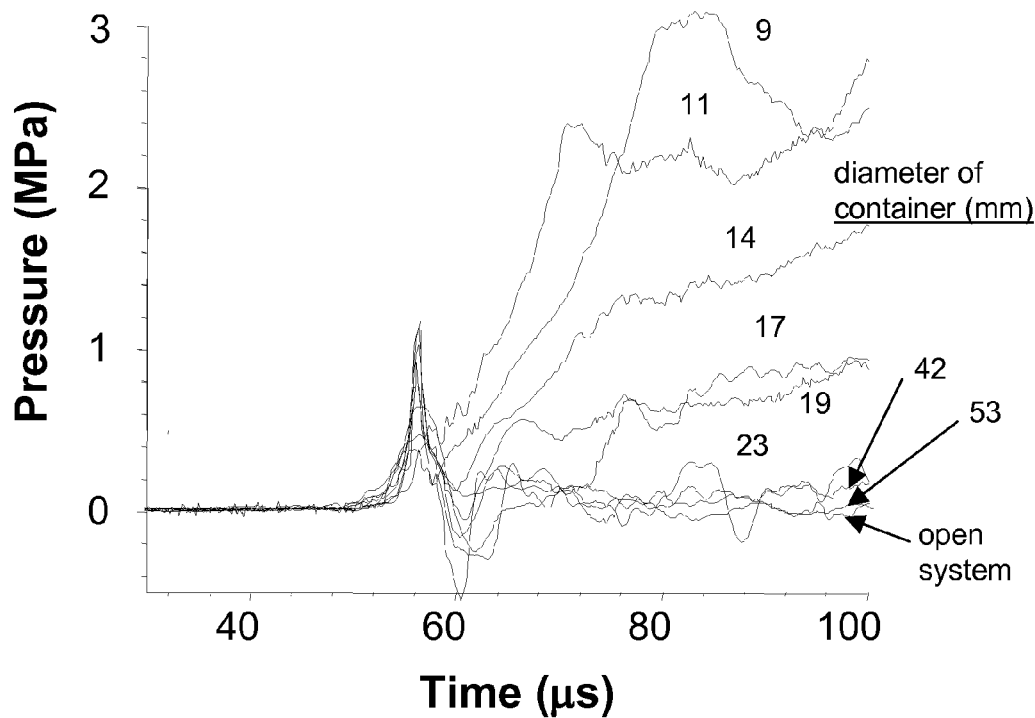
Figure 21:
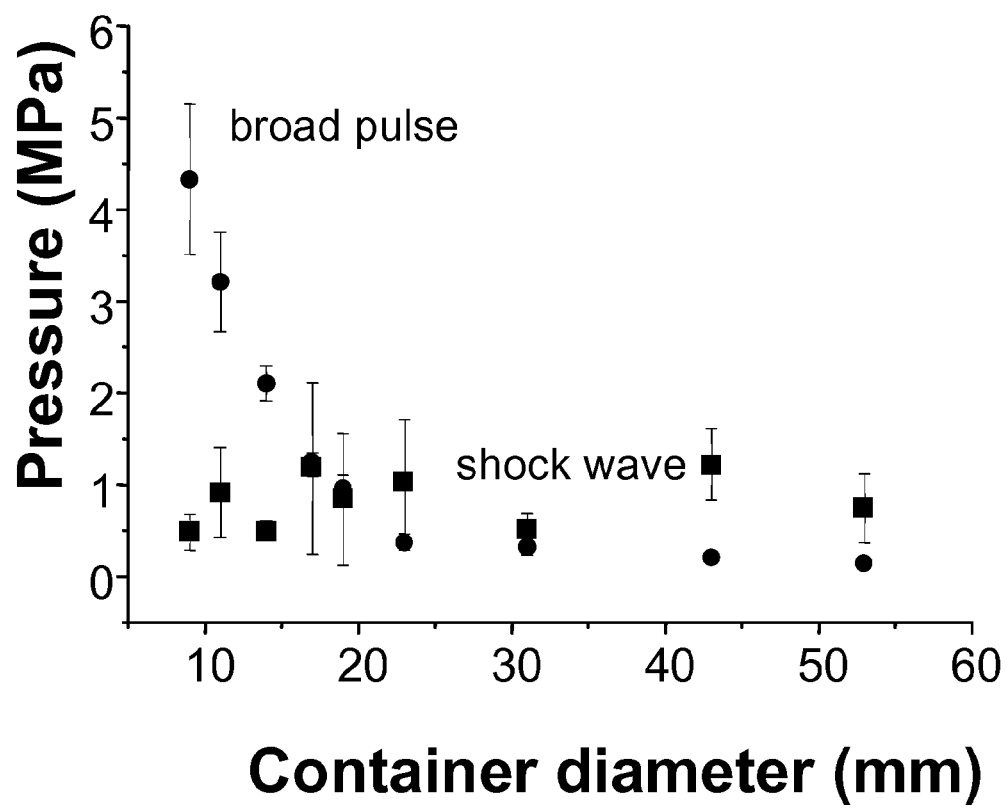
FIG. 21 is a graph showing the effect of water container diameter on the peak pressures generated by the prototype cell transfection devices.

The pressure profiles measured during this experiment are summarized in FIGS. 20A and 20B. All the profiles, regardless of the diameter of the container, contain the same high-frequency shock wave component that is observed in open systems. However, at the smaller confinement volume diameters, a broad pressure pulse also occurs that results from the expansion of solid and gas products from the combustion of the nanoenergetic materials. When the diameter of the confinement volume goes below about 20 mm, the broad pressure pulse is the dominant energy that is seen by the pressure sensor. FIG. 21 is a graph of the peak pressures measured during the shock wave portion of the pressure profile and during the subsequent broad pressure pulse, illustrating that the broad pressure pulse dominates the pressure profile for containers with a diameter of less than about 20 mm.

Figure 22:
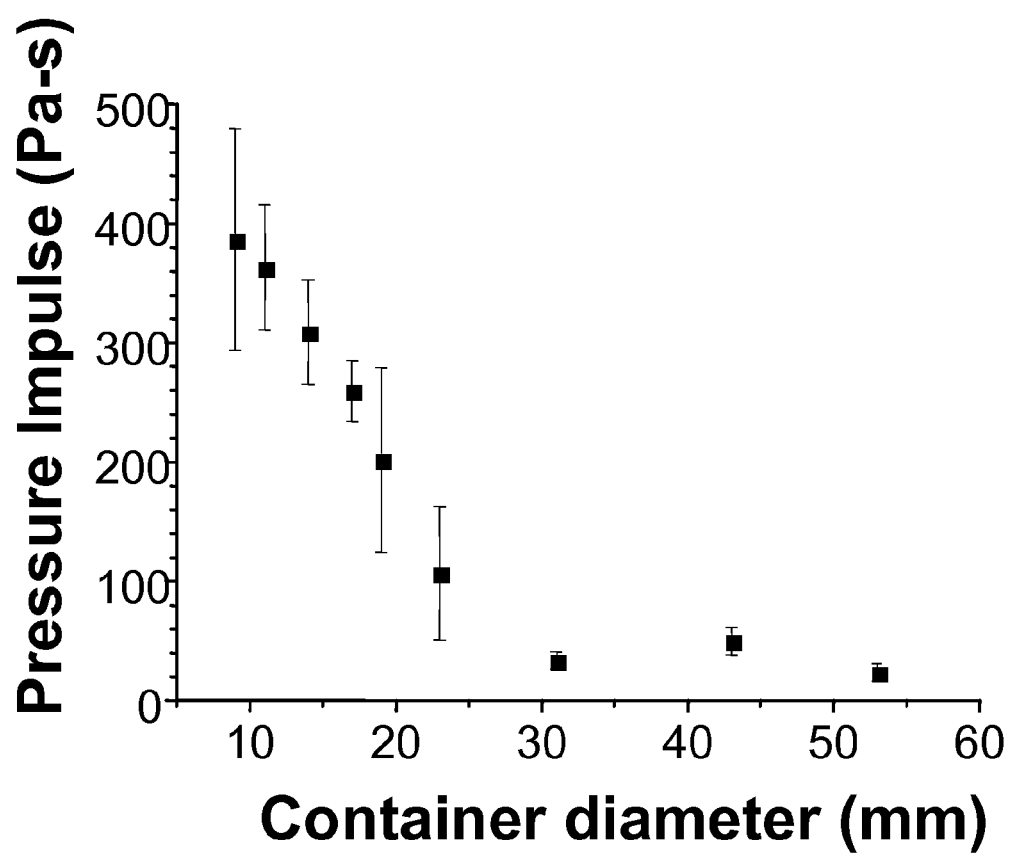
FIG. 22 is a graph showing the effect of water container diameter on the pressure impulses generated by the prototype cell transfection devices.

FIG. 22 is a graph summarizing the pressure impulse calculated from the pressure profiles measured at different water container diameters. The pressure impulse increases sharply at water container diameters less than about 20 mm due to the increasing influence of the broad pressure pulse. At water container diameters above about 20 mm, the pressure impulse is independent of diameter because the pressure profiles are dominated by the shock wave profile, which is relatively independent of the container diameter.

The results of this experiment demonstrated that the peak pressures due to shock waves experienced by cells or tissues were dependent upon the diameter of the fluid vessel in which the cells would be subjected to the shock wave. For larger diameter containers, the peak pressure due to the shock wave is the dominant feature of the pressure profile, and is relatively insensitive to the size of the container above a threshold container diameter of about 20 mm. For smaller containers with a diameter of less than about 20 mm, the broad pressure pulse due to the expansion wave of detonation by-products dominates the pressure profile. The peak pressure induced by the broad pressure pulse strongly depends on the diameter of the container below a diameter of about 20 mm and increases sharply as the container diameter approaches zero.

Example 10

Efficacy of Prototype Cell Transfection Device was Compared to Existing Transfection Methods To evaluate the efficacy of the prototype cell transfection device in comparison to existing transfection methods, the following experiment was conducted. The transfection rate in embryonic chicken heart cells using the prototype cell transfection device was compared with commercially available chemical methods (cationic lipid based reagents) and physical methods (electroporation).

Embryonic chicken heart cells were obtained from chick embryos raised in the lab. Chick embryos were obtained from fertilized White Leghorn eggs (Hy-Line W-36, Hy-Line North America, LLC, West Des Moines, Iowa) and incubated for five days at 38° C. and 80% humidity. Stage 25 embryos (Hamburger; Hamilton 1951) were removed from the egg and placed in a modified Tyrode solution of 140 mM NaCl, 5.6 mM KCl, 1.85 mM $CaCl_2$, 0.5 mM $MgCl_2$, 10 mM $NaHCO_3$, 1.8 mM $NaH_2PO_4$, 5.5 mM Glucose, at 37° C. and gassed with a mixture of 95% $O_2$ and 5% $CO_2$, with a pH of 7.3-7.4. The hearts were then separated from the embryo and processed for single cell dissociation.

The cells were dissociated from the atrium or ventricle with Papain (Worthington, Lakewood, N.J.) according to the manufacturer's protocol. Briefly, Papain was activated for 30 min. at 37° C. by the addition of β-mercaepthanol, ethylendiaminetetraacetic acid (EDTA) and L-cystein. Atrial and ventricular tissues were incubated in a Papain solution in a Hanks Balanced Salt (HBBS) solution of $Ca^{2+}$ and $Mg^{2+}$ free for 5 to 10 minutes. The Papain was then inactivated by the addition of a cold HBBS containing 1 mg/ml trypsin inhibitor soybean, followed by washing the tissue/cells twice with a cell culture medium. Cells were dissociated by pipetting the tissue 5 to 10 times through a small diameter end-fire-polished glass Pasteur pipette. If the tissue was dissociated into single cells before the washing step, the cells were pelleted by centrifugation at 800 g for 3 to 5 minutes.

An average of $10^3$ cells were used for each transfection experiment. A sample of each batch of cells was used to evaluate cell condition using Trypan Blue staining and a hematocytometer to quantify the percentage of viable cells in each cell suspension prior to transfection.

Plasmids containing the information to express EGFP (enhanced green fluorescent protein) under the control of CMV (human cytomegalovirus immediate early gene) promoter were transfected directly into the suspended cells using the prototype cell transfection device. This plasmid, when transfected into and expressed by living cells, induces the production of fluorescent green EGFP inside the cells.

Prototype cell transfection devices were assembled as illustrated in FIG. 5, using methods similar to those described in Example 7. The target vessel was a stainless steel cylinder with a diameter of 8 mm and a height of 10 mm. A pressure transducer (PCB 134A02) was mounted in the bottom surface of the target vessel to monitor pressure inside the vessel during transfection.

A suspension containing 103 chicken cardiac cells was transfected with 0.5 µg of the plasmids using the prototype cell transfection device loaded with 3 mg of $Bi_2O_3$/Al nanoenergetic material. For these transfections, the average peak pressure was 23.8 MPa, and the average pressure impulse was 1,258 Pa-s. For comparison, transfections were performed on additional chicken cardiac cell suspensions using existing transfection methods: SiPNF (SiPortNeoFx), SiPAm (SiPortAmine), Lip-2000 (Lipofectamine 2000), Lip-LTX (Lipofectamine LTX), T-LT1 (Transit LT1), and electroporation (Electro).

After the transfection procedures, the cell suspensions were transferred into 35 mm culture dishes with an insert of a circular 25 mm glass cover slip (Fisher Scientific). For the cell cultures, the cells were seeded in the glass cover slip for 1-2 hr into the incubator to allow the cells to attach to the substrate. Then cell culture dish was carefully filled with 2 ml of fresh culture media and kept it in the incubator with an atmosphere of 10% $CO_2$ for 24 hrs.

The number of dead or dying cells in the transfected cardiac cell suspensions was assessed using the vital dyes Trypan Blue, Orange Nucleic Acid Stain, Hoechst 33258, and YO-PRO-1. Viability of the transfected cardiac cells was assessed using the cell-permeant dye calcein AM. The general health of the transfected cells was assessed using an EdU (5-ethynyl-2'-deoxyuridine) cell proliferation assay (Click-iT, Invitrogen).

Figure 23:
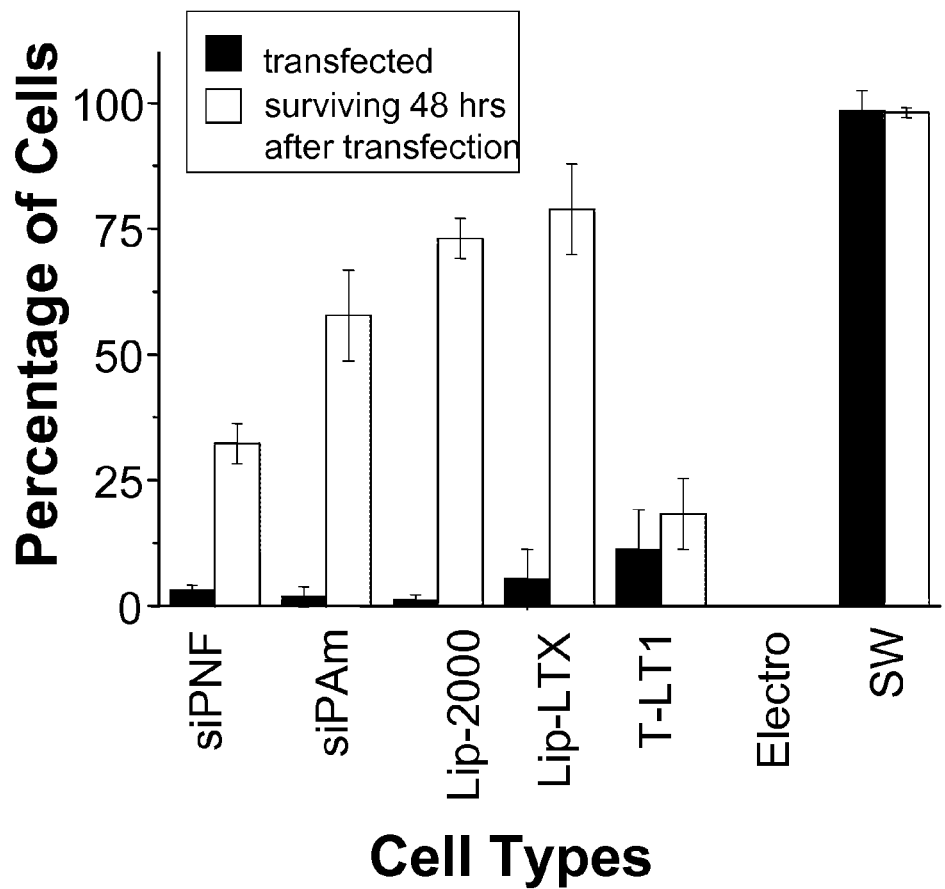
FIG. 23 is a graph summarizing the transfection rate and survival rate of a variety of transfected cell types.

FIG. 23 is a summary of the results of the transfections of the chicken cardiac cells described above. The prototype cell transfection device (SW) using shock waves produced transfection and survivability rates in excess of 99%. None of the existing transfection methods resulting in a transfection rate of greater than about 10%. Further, the survivability of the cells transfected using existing methods ranged from 0% (electroporation) to about 80% (Lip-LTX). The results obtained using the prototype cell transfection device were far superior to results obtained with the other existing transfection methods. Although these cell viability analyses were performed 48 hrs after transfection, viable healthy cells were observed for up to a month after transfection.

To further assess any potential damage to the cardiac cells by the transfection process the electrical properties of the transfected cardiac cells were compared to the control cells. Table 3 is a summary of the electrical measurements performed on the cells. The electrical properties of the transfected cardiac cells did not significantly differ from the electrical properties of the control cardiac cells.

TABLE 3

Effect of Transfection on the Electrophysiology of Cardiac Cells.

| Cardiac cell sample | Vmax (V/sec) | Amplitude (mV) | Duration (msec) | RMP (mV) |
|---|---|---|---|---|
| Control | 33 ± 6.2 | 108 ± 0.7 | 116 ± 1.2 | 60 ± 0.9 |
| Transfected | 32 ± 4.6 | 110 ± 0.3 | 118 ± 0.9 | 61 ± 0.6 |

The results of this experiment demonstrated that efficacy of the prototype cell transfection device using shock waves induced by the combustion of nanoenergetic materials transfected chicken cardiac cells with over 99% efficiency and over 99% survivability, far in excess of existing transfection methods.

Example 11

Prototype Cell Transfection Device Used to Assess Effect of Shock Wave Strength on the Transfection of Different Cell Types To evaluate the effect of higher peak pressures and higher pressure impulses on the efficacy of the prototype cell transfection device on a variety of living cell types, the following experiment was conducted. A variety of cell types were transfected using the prototype cell transfection device: cell cancer cell lines including adenocarcinoma epithelial cells (Hela), promyelocytic leukemia (HL-60), colonrectal adenocarcinoma (HT-29), as well as plant cells from *Arabidopsis* spp. (ARA).

The cell lines Hela, HL-60, and HT-29 (ATCC; Manassas, Va.) were propagated and cultured as recommended by the ATCC. The adherent cells were resuspended in 10 ml TrypLE Express (Gibco, Invitrogen) for 10 minutes. The cells were then pelleted by centrifugation at 800 g for 5 minutes, washed 3 times, and resuspended with the media recommended by ATCC. An average of 103 cells were used for each transfection experiment. A sample of each batch of cells was used to evaluate cell condition using Trypan Blue staining and a hematocytometer to quantify the percentage of viable cells in each cell suspension prior to transfection.

Figure 24:
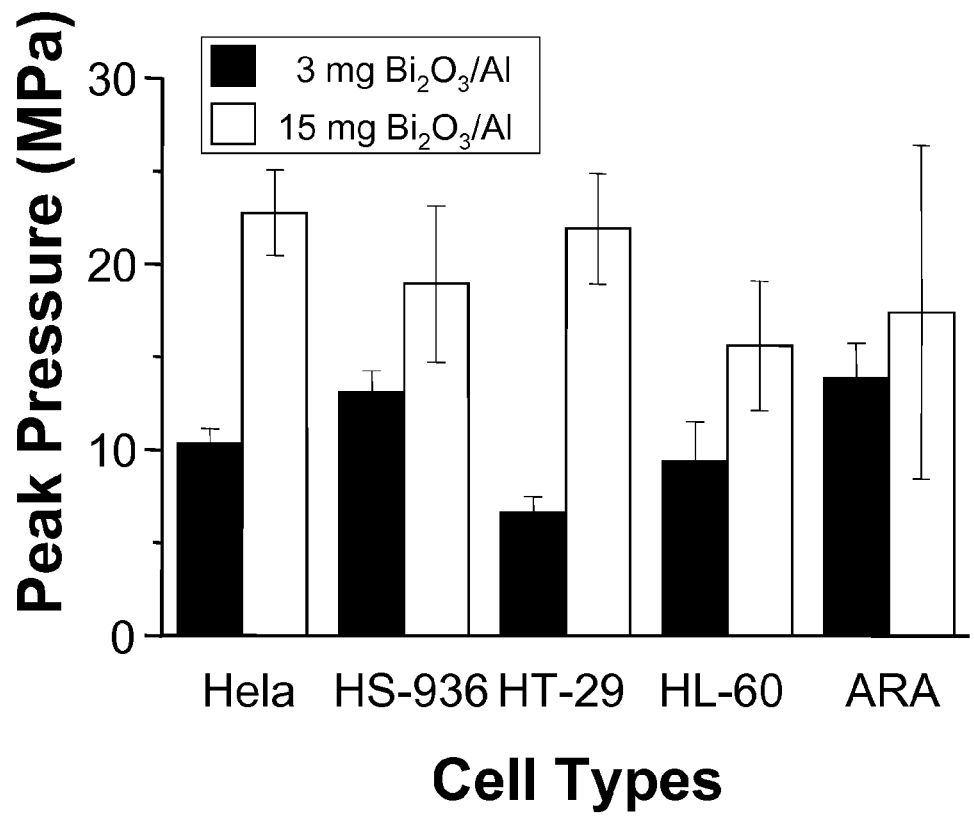
FIG. 24 is a graph summarizing the peak pressures generated by prototype cell transfection device with two masses of nanoenergetic material for each of the cell types transfected.
Figure 25:
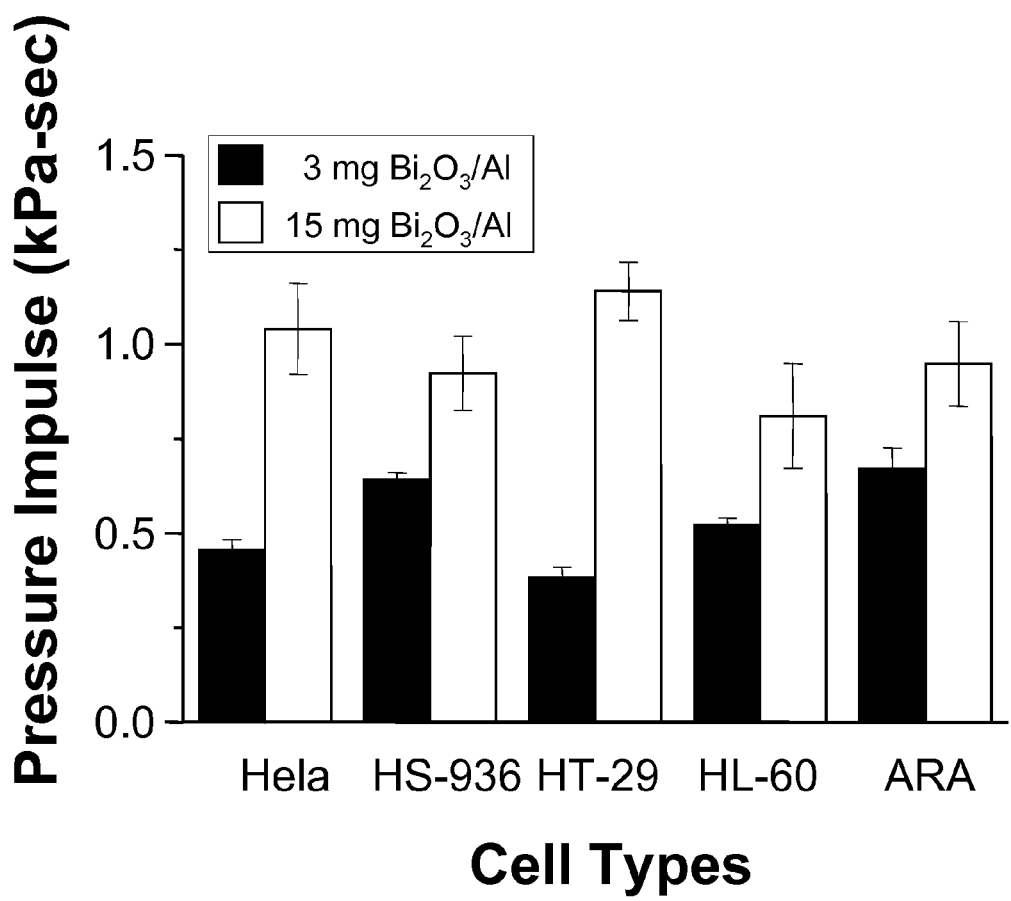
FIG. 25 is a graph summarizing the pressure impulses generated by prototype cell transfection device with two masses of nanoenergetic material for each of the cell types transfected.

All cells suspended and loaded into a prototype cell transfection device using similar methods to those described in Example 10. Two different shock wave intensities were used for the transfections of this experiment, corresponding to the combustion of 3 mg and 15 mg of $Bi_2O_3$/Al nanoenergetic material. FIGS. 24 and 25 summarize the peak pressures and pressure impulses, respectively, measured during the transfection of the different cell types.

Figure 26:
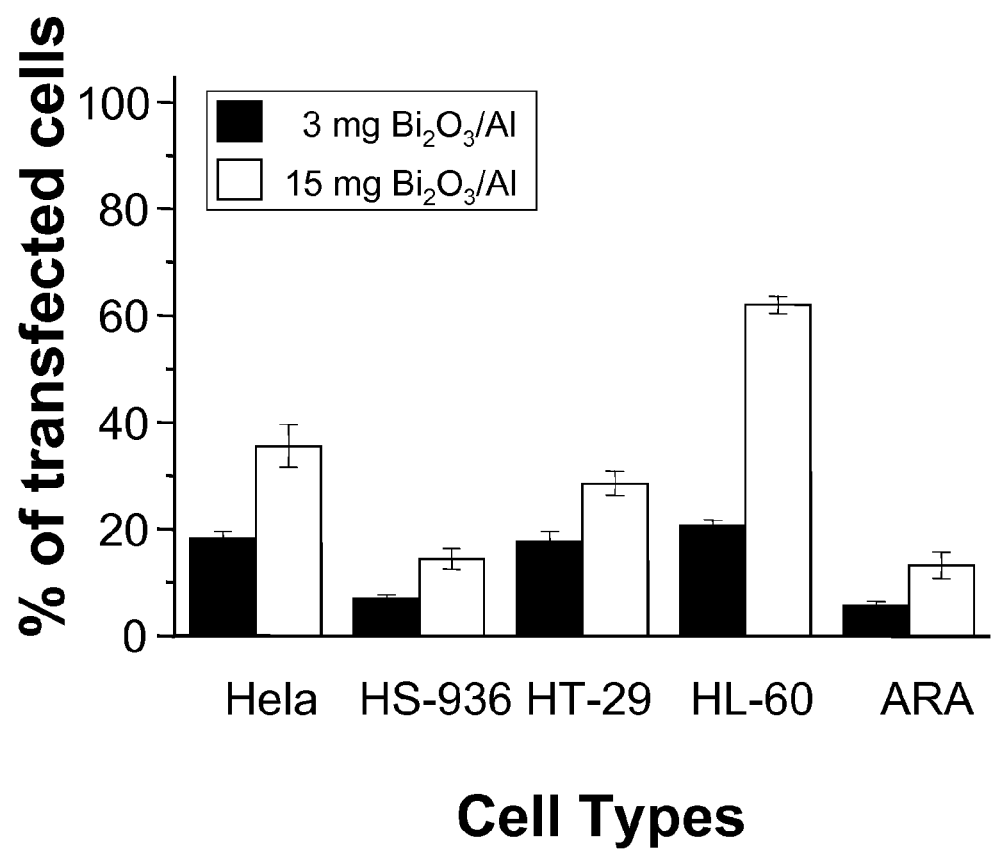
FIG. 26 is a graph summarizing the effect of the amount of nanoenergetic material used in the miniature shock wave generating device on transfection rate and survival of a variety of transfected cell types.

FIG. 26 summarizes the percentage of cells in each cell suspension that were successfully transfected using the prototype cell transfection device. For most cell types, increasing the shock wave intensity roughly doubled the percentage of transfected cells; the percentage of transfected HL-60 cells roughly tripled with the higher shock wave intensity. Overall, the percentages of cells transfected is much lower than the percentages of cardiac cells transfected, as described in Example 10.

The survival and viability of the transfected cells was evaluated using methods similar to those described in Example 10. For all cell types and shock wave intensities, more than 99% of the transfected cells survived and were viable.

The results of this experiment demonstrated that the prototype cell transfection device transfects a wide diversity of cell types with excellent post-transfection survival and viability.

What is claimed is:

1. A miniature device for creating and directing at least one shock wave into biological targets, wherein the at least one shock wave has a peak pressure of up to 200 MPa and a duration of up to 100 microseconds, the device comprising:
    a. an amount of nanoenergetic material; and,
    b. a transmissive barrier, whereby the barrier propagates the at least one shock wave and prevents byproducts of combustion of the nanoenergetic material from contacting the biological targets.

2. The device of claim 1, wherein the nanoenergetic material comprises a nanostructured mixture comprising a plurality of fuel nanoparticles selected from the group comprising aluminum, boron, beryllium, hafnium, lanthanum, lithium, magnesium, neodymium, silicon, tantalum, thorium, titanium, yttrium, zirconium, and combinations thereof, and a plurality of oxidizer nanoparticles selected from the group comprising copper oxide, silver oxide, bismuth oxide, cobalt oxide, chromium oxide, iron oxide, mercuric oxide, iodine oxide, manganese oxide, molybdenum oxide, niobium oxide, nickel oxide, lead oxide, palladium oxide, silicone oxide, tin oxide, tantalum oxide, titanium dioxide, uranium oxide, vanadium oxide, tungsten oxide, and combinations thereof.

3. The nanoenergetic material of claim 2, wherein the weight ratio of fuel to oxidizer is about 1.4 to about 1.8.

4. The device of claim 1 wherein the transmissive barrier comprises a material with a density ranging between about 0.8 and about 1.2 g/cm$^3$.

5. The device of claim 1, wherein the transmissive barrier is selected from the group consisting of a flexible membrane, a solid member, a gel, a liquid, and combinations thereof.

6. The device of claim 5, wherein the gel is selected from the group consisting of a Type A gelatin, Type B gelatin, a hydrogel, and combinations thereof, and wherein the gel has a strength ranging between about 50 and about 350 on a Bloom scale.

7. The device of claim 5, wherein the thickness of the flexible membrane ranges between about 0.01 mm and about 5 mm.

8. The device of claim 1, wherein the miniature device further comprises a substrate, an igniter, and a tubular member.

9. The device of claim 8, wherein the substrate comprises a rigid planar sheet comprising opposed surfaces, and wherein the maximum dimension of the substrate ranges between about 10 mm and about 50 mm and the thickness of the substrate is less than about 10 mm.

10. The device of claim 8, wherein the tubular member forms a lumen, wherein the lumen is filled with the transmissive barrier, and wherein the transmissive barrier is a gel.

11. The device of claim 10, wherein the gel is selected from the group consisting of Type A gelatin, Type B gelatin, hydrogel, and combinations thereof, and wherein the gel has a density ranging between about 0.8 and about 1.2 g/cm$^3$ and a strength ranging between about 50 and about 350 on a Bloom scale.

12. The device of claim 8, wherein the tubular member has a diameter ranging between about 1 mm and about 10 mm, and a length ranging between about 1 mm and about 100 mm.

13. The device of claim 8, wherein one surface of the substrate further contains at least one well, whereby the at least one well holds the amount of nanoenergetic material.

14. The device of claim 1, wherein the miniature device further comprises an additional transmissive barrier and wherein the additional transmissive barrier is a flexible membrane with a density ranging between about 0.8 and about 1.2 g/cm$^3$ and a thickness ranging between about 0.01 mm and about 5 mm.

15. A miniature device for creating and directing at least one shock wave into biological targets, wherein the at least one shock wave has a peak pressure of up to 200 MPa and a duration of up to 100 microseconds, the device comprising:
    a. a substrate comprising opposed surfaces;
    b. at least one igniter bonded to one of the surfaces of the substrate;
    c. an amount of nanoenergetic material placed on one of the surfaces of the substrate in contact with the at least one igniter; and,
    d. a transmissive barrier placed in close proximity to the amount of nanoenergetic material opposite the surface.

16. The device of claim 15, wherein the substrate comprises a rigid planar sheet, and wherein the maximum dimension of the substrate ranges between about 10 mm and about 50 mm, and the thickness of the substrate is less than about 10 mm.

17. The device of claim 15, wherein the nanoenergetic material comprises a nanostructured mixture comprising a plurality of fuel nanoparticles selected from the group comprising aluminum, boron, beryllium, hafnium, lanthanum, lithium, magnesium, neodymium, silicon, tantalum, thorium, titanium, yttrium, zirconium, and combinations thereof, and a plurality of oxidizer nanoparticles selected from the group comprising copper oxide, silver oxide, bismuth oxide, cobalt oxide, chromium oxide, iron oxide, mercuric oxide, iodine oxide, manganese oxide, molybdenum oxide, niobium oxide, nickel oxide, lead oxide, palladium oxide, silicone oxide, tin oxide, tantalum oxide, titanium dioxide, uranium oxide, vanadium oxide, tungsten oxide, and combinations thereof.

18. The nanoenergetic material of claim 17, wherein the weight ratio of fuel to oxidizer is about 1.4 to about 1.8.

19. The device of claim 15, wherein the amount of the nanoenergetic material ranges between about 0.1 mg and about 20 mg.

20. The device of claim 15, wherein the transmissive barrier comprises a material with a density ranging between about 0.8 and about 1.2 g/cm$^3$.

21. The device of claim 15, wherein the transmissive barrier is selected from the group consisting of a flexible membrane, a solid member, a gel, a liquid, and combinations thereof.

22. The device of claim 21, wherein the gel is selected from the group consisting of Type A gelatin, Type B gelatin, hydrogel, and combinations thereof, and wherein the gel has a strength ranging between about 50 and about 350 on a Bloom scale.

23. The device of claim 21, wherein the thickness of the flexible membrane ranges between about 0.01 mm and about 5 mm.

24. The device of claim 21, wherein the miniature device further comprises a tubular member forming two opposed openings and a lumen, wherein the tubular member has an outer diameter ranging between about 1 mm and about 10 mm, and a length ranging between about 1 mm and about 100 mm, wherein the lumen is filled with gel, and wherein one opening is placed in close proximity to the nanoenergetic material opposite the surface.

25. The device of claim 21, wherein the flexible membrane is adhered to one surface of the substrate, wherein the amount of nanoenergetic material is placed between the flexible membrane and the surface.

26. The device of claim 15, wherein one surface of the substrate defines the walls of at least one well, wherein the volume of each well ranges between about $0.1$ mm$^3$ and about $6$ mm$^3$, and wherein the at least one well contains the amount of nanoenergetic material.

27. The device of claim 15, wherein one surface of the substrate forms a concave surface.

28. A miniature device for creating and directing at least one shock wave into biological targets, wherein the at least one shock wave has a peak pressure of up to 200 MPa and a duration of up to 100 microseconds, the device comprising:
   a. a substrate comprising opposed surfaces;
   b. at least one igniter bonded to one surface of the substrate;
   c. an amount of nanoenergetic material placed on the surface of the substrate in contact with the at least one igniter;
   d. at least one tubular member forming opposed openings and a lumen, and wherein one opening is placed in close proximity to the nanoenergetic material opposite to the surface of the substrate; and,
   e. a gel placed inside the lumen of the at least one tubular member.

29. The device of claim 28, wherein the tubular member has an outer diameter ranging between about 1 mm and about 10 mm, and a length ranging between about 1 mm and about 100 mm.

30. The device of claim 28, wherein the gel is selected from the group consisting of Type A gelatin, Type B gelatin, hydrogel, and combinations thereof, and wherein the gel has a density ranging between about 0.8 and about 1.2 g/cm$^3$ and gel strength ranging between about 50 and about 350 on a Bloom scale.

31. A miniature device for creating and directing at least one shock wave into biological targets, wherein the at least one shock wave has a peak pressure of up to 200 MPa and a duration of up to 100, the device comprising:
   a. a substrate comprising an upper and a lower surface;
   b. at least one igniter bonded to the upper surface of the substrate layer;
   c. an amount of nanoenergetic material placed on the upper surface of the substrate in contact with the at least one igniter; and,
   d. a flexible membrane bonded to one surface of the substrate over the amount of nanoenergetic material.

32. The device of claim 31 wherein the flexible membrane comprises a material with a density ranging between about 0.8 and about 1.2 g/cm$^3$, and a thickness ranging between about 0.01 and about 5 mm.

* * * * *

UNITED STATES PATENT AND TRADEMARK OFFICE
CERTIFICATE OF CORRECTION

| | | |
|---|---|---|
| PATENT NO. | : 8,303,522 B2 | |
| APPLICATION NO. | : 12/253706 | |
| DATED | : November 6, 2012 | |
| INVENTOR(S) | : Steve Apperson et al. | |

It is certified that error appears in the above-identified patent and that said Letters Patent is hereby corrected as shown below:

Col. 24, line 12 (Claim 14, line 3): "barrieris" should read --barrier is--

Signed and Sealed this
Twelfth Day of February, 2013

Teresa Stanek Rea
*Acting Director of the United States Patent and Trademark Office*